US006815159B2

(12) United States Patent
Thibeault et al.

(10) Patent No.: US 6,815,159 B2
(45) Date of Patent: Nov. 9, 2004

(54) PURIFIED ACTIVE HCV NS2/3 PROTEASE

(75) Inventors: Diane Thibeault, Laval (CA); Daniel Lamarre, Laval (CA); Roger Maurice, Laval (CA); Louise Pilote, Laval (CA); Armin Pause, Laval (CA)

(73) Assignee: Boehringer Ingelheim (Canada) Ltd., Laval (CA)

( * ) Notice: Subject to any disclaimer, the term of this patent is extended or adjusted under 35 U.S.C. 154(b) by 293 days.

(21) Appl. No.: 10/017,736

(22) Filed: Dec. 14, 2001

(65) Prior Publication Data

US 2002/0192640 A1 Dec. 19, 2002

Related U.S. Application Data

(60) Provisional application No. 60/256,031, filed on Dec. 15, 2000.

(51) Int. Cl.$^7$ .............................. C12Q 1/70; C12N 9/99; C12N 9/96; C12N 9/60; C07K 1/06; C07K 1/08

(52) U.S. Cl. .......................... 435/5; 435/184; 435/188; 435/219; 435/23; 530/412

(58) Field of Search ...................... 530/412; 435/235.1, 435/239, 184, 188, 219, 5, 23

(56) References Cited

U.S. PATENT DOCUMENTS 5,714,371 A * 2/1998 Ramanathan et al. ....... 435/219

FOREIGN PATENT DOCUMENTS

| WO | WO 97/08304 | 3/1997 |
| WO | WO 99/07733 | 2/1999 |
| WO | WO 01/16379 | 3/2001 |
| WO | WO 01/68818 | 9/2001 |

OTHER PUBLICATIONS

Chirgwin, Przybyla et al.; Isolation of Biologically Active Riboncleic Acid from Sources Enriched in Ribonuclease; Biochemistry; 1979, v. 18; 5294–5299.
Darke, Jacobs et al.; Inhibition of Hepatitis C Virus NS2/3 Procession by NS4A Peptides; J. Biol. Chem.; 1999, V. 274, No. 49; 34511–34514.
Grakoui, McCourt et al.; A second hepatitis C virus–encoded proteinase; Proc. Natl. Acad. Sci. USA; 1993, V. 90; 10583–10587.
Kolykhalvo, Mihalik et al.; Hepatitis C Virus–Encoded Enzymatic Activites and Conserved RNA Elements in the 3' Nontranslated Region are Essential for Virus Replication In Vivo; 2000, V. 74, No. 4; 2046–2051.
Lin, Timasheff; On the role of surface tension in the stabilization of globular proteins; Protein Sci.; 1996, V. 5; 372–381.
Liu, Bhat et al.; The Hepatitis C Virus NS2 Protein Generated by NS2–3 Autocleavage is Required for NS5A Phosphorylation; Biochem. Biochem. Biophys. Res. Commun.; 1999, V. 254; 572–577.

Neddermann, Clementi et al.; Hyperphosphorylation of the Hepatitis C Virus NS5A Protein Requires an Active NS3 Protease, NS4A, NS4B, and NS5A Encoded on the Same Polyprotein; J. Virol.; 1999, V. 73, No. 12: 9984–9991.
Pallaoro, Lahm et al.; Characterization of the Hepatitis C Virus NS2/3 Processing Reaction by Using a Purified Precursor Protein; J. Virol.; 2001, V. 75, No. 20; 9939–9946.
Pieroni, Santolini et al.; In Vitro Study of the NS2–3 Protease of Hepatitis C Virus; J. Virol.; 1997, V. 71, No. 9; 6373–6380.
Reed, Grakoui et al.; Hepatitis C Virus–Encoded NS2–3 Protease: Cleavage–Site Mutagenesis and Requirements for Bimolecular Cleavage; J. Virol.; 1995, V. 69, No. 7; 4127–4136.
Santolini, Pacini et al.; The NS2 Protein of Hepatitis C Virus is a Transmembrane Polypeptide; J. Virol.; 1995, V. 69, No. 12; 7461–7471.
Thibeault, Maurice et al.; In Vitro Characterization of a Purified NS2/3 Protease Variant of Hepatitis C Virus; J. Biol. Chem.; 2001, V. 276, No. 49; 46678–46684.
Walker, M.A.; Hepatitis C virus: an overview of current approaches and progress; Drug Discovery Today; 1999; V. 4, No. 11; 518–529.
Dymock, Jones et al.; Novel approaches to the treatment of hepatitis C virus infection; Antiviral Chemistry & Chemotherapy; 2000; V. 11(2); 79–96.
Gorbalenya, Snijder; Viral cysteine proteinases; Perspect. Drug Discovery Design; 1996; V. 6; 64–86.
Hijikata, Mizushima et al.; Two Distinct Proteinase Activities Required for the Poscessing of a Putative Nonstructural Precursor Protein of Hepatitis C Virus; J. Virol; 1993; V. 67, No. 8; 4665–4675.
Hirowatari, Hijikata et al.; Two proteinase activities in HCV polypeptide expressed in insect cells using baculovirus vector; Arch. Virol.; 1993; V. 133; 349–356.
Komoda, Hijikata et al.; Processing of hepatitis C viral polyprotein in Escherichia coli; Gene; 1994; V. 145; 221–226.

(List continued on next page.)

* cited by examiner

Primary Examiner—Mary E. Mosher
(74) Attorney, Agent, or Firm—Robert P. Raymond; Susan K. Pocchiari; Mary-Ellen M. Devlin

(57) ABSTRACT

A method for producing a refolded, inactive form of recombinantly produced NS2/3 protease which comprises the steps of: a) purifying the protease from inclusion bodies in the presence of a chaotropic agent; and b) refolding the purified protease by contacting it with a reducing agent and lauryldiethylamine oxide (LDAO) in the presence of reduced concentration of chaotropic agent or polar additive. The invention further comprises a method for activating this refolded inactive NS2/3 protease by adding an activation detergent. This method produces large amounts of the active NS2/3 protease to allow small molecules and ligands to be screened as potential inhibitors of NS2/3 protease, which may be useful as therapeutic agents against HCV.

37 Claims, 12 Drawing Sheets-

OTHER PUBLICATIONS

Wada, Wada et al.; Codon usage tabulated from the GenBank genetic sequence data; Nuc. Acids Research; 1992; V. 20; 2111–2118.

Wong, Albright, et al.; Immobilized Metal Ion Affinity Chromatography (IMAC)—Chemistry and Bioseparation Applications; Separation and Purification Methods; 1991; V. 20(1); 49–106.

Ausubel, Brent et al.; Current Protocols in Molecular Biology; 1994; vol. 1,2,3 and 4; Wiley, New York.

Sambrook, Fritsch et al.; Molecular Cloning—A Laboratory Manual, Second Edition; 1989; Cold Spring Harbor Laboratory Press.

Chemello, Cavalletto et al.; The effect of interferon alfa and ribavirin combination therapy in naïve patients with chronic hepatitis C; J. Hepatology; 1995; V. 23. Suppl. 2; 8–12.

Wenzel, Troxell et al.; Establishment of a Cell–Based Assay for Evaluation of Compounds against HCV NS2–3 Protease Activity; Prog. & Abstr. Interscience Conf. Antimicrobial Agents & Chemo.; 199; V. 39; 409.

FIGURE 1A

NUCLEOTIDE SEQUENCE OF NS2/3 (810-1206) ST (SEQ ID. No. 1)

```
atggaccggg agatggctgc atcgtgcgga ggcgcggttt tcataggtct tgcactcttg
accttgtcac catactataa agtgctcctc gctaggctca tatggtggtt acagtattta
atcaccagag tcgaggcgca cttgcaagtg tggatcccc ctctcaatgt tcggggaggc
cgcgatgcca tcatcctcct cacgtgcgca gtccacccag agctaatctt tgacatcacc
aaactcctgc tcgccatatt cggtccgctc atggtgctcc aggcaggcat aaccaaagtg ccgtac
ttcgtgcgtg cgcaggggct cattcgtgcg tgtatgttgg tgcggaaggc tgcgggggt
cattatgtcc aaatggcctt catgaagcta gctgcgctga caggtacgta cgtttatgac
catctcactc cattgcagga ttgggcccac gcgggcctac gagaccttgc agtggcggta
gagcccgtca tcttctctga catggaggtc aagatcatca cctgggggc ggacaccgcg
gcatgcgggg acatcatttc aggtctgccc gtctccgctc gaaggggaag ggagatactc
ctgggaccgg ccgataattt tgaagggcag gggtggcgac tccttgcgcc catcacggcc
tactcccaac agacacgggg cctacttggt tgcatcatca ccagcctcac aggccgggac
aagaaccagg tcgaggggga ggttcaagtg gtctccaccg ctacacaatc tttcctggcg
acctgcgtca acggcgtgtg ttggactgtc ttccatggcg ccggctcaaa gaccttggcc
ggccccaaag gcccaatcac ccagatgtac actaatgtgg accaggacct cgtcggctgg
caggcgcccc ctggggcgcg ctccatgaca ccatgcacct gcggcagctc ggacctctat
ttggtcacga gacatgccga cgtcattccg gtgcgccggc ggggcgacag tagggggagc
ctgctctccc ccaggcctgt ctcctacttg aagggctctt cgggtggccc actgctctgc
ccttcggggc acgttgtggg catcttccgg gctgctgtgt gcacccgggg ggttgcaaaa
gcggtggact tcatacctgt tgagtctatg gaaactacca tgcggactag tagcgcttgg
cgtcacccgc agttcggtgg t
```

FIGURE 1B

AMINO ACID SEQUENCE OF NS2/3 (810-1206)-ST (SEQ ID NO. 2)

```
MDREMAASCG GAVFIGLALL TLSPYYKVLL ARLIWWLQYL ITRVEAHLQV WIPPLNVRGG RDAIILLTCA
VHPELIFDIT KLLLAIFGPL MVLQAGITKV PYFVRAQGLI RACMLVRKAA GGHYVQMAFM KLAALTGTYV
YDHLTPLQDW AHAGLRDLAV AVEPVIFSDM EVKIITWGAD TAACGDIISG LPVSARRGRE ILLGPADNFE
GQGWRLLAPI TAYSQQTRGL LGCIITSLTG RDKNQVEGEV QVVSTATQSF LATCVNGVCW TVFHGAGSKT
LAGPKGPITQ MYTNVDQDLV GWQAPPGARS MTPCTCGSSD LYLVTRHADV IPVRRRGDSR GSLLSPRPVS
YLKGSSGGPL LCPSGHAVGI FRAAVCTRGV AKAVDFIPVE SMETTMRTSS AWRHPQFGG
```

FIGURE 2
A. *in vitro* translated N-terminal deletion mutants
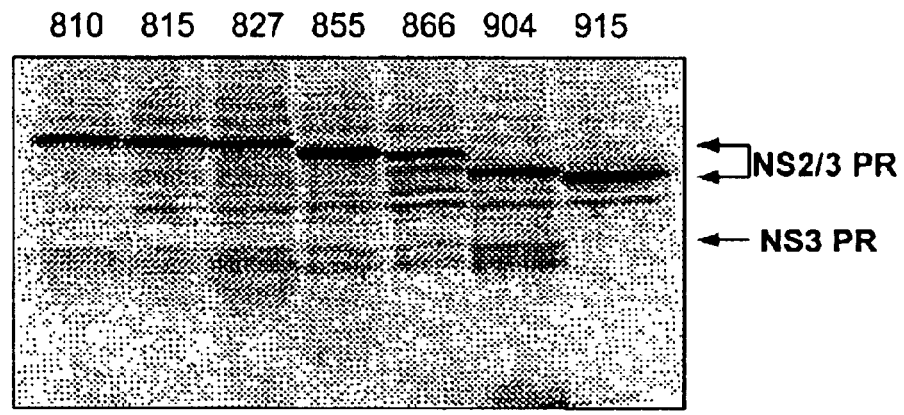
B. *E. coli* expression - SDS-PAGE
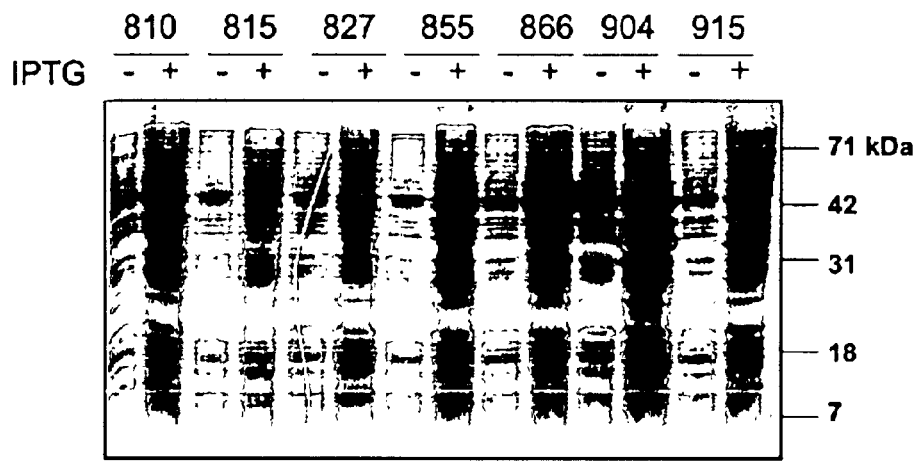
C. *E. coli* expression - Immunoblot with anti-NS3
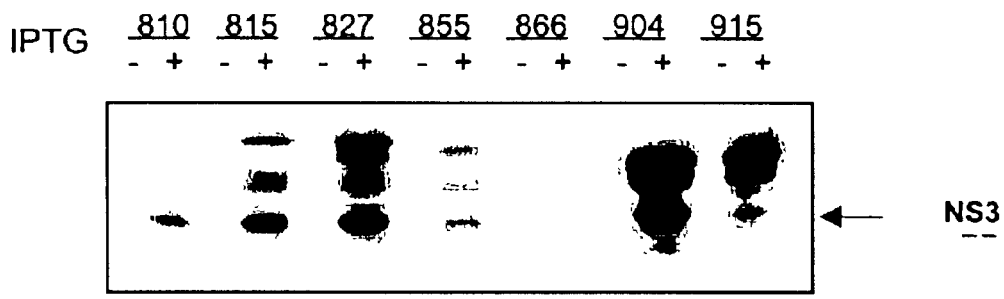

4k 6H NS2/3(904-1206)-ST-4K

FIGURE 7
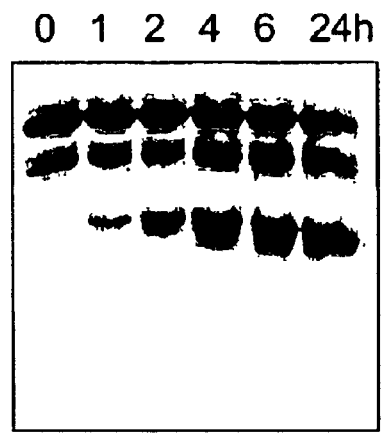
A. anti-NS3
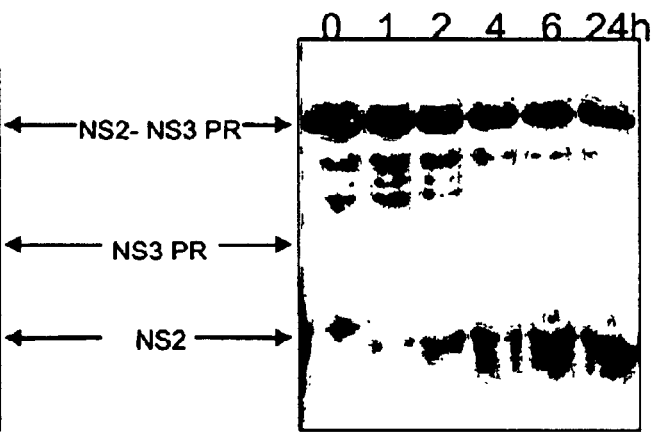
B. anti-His6
FIGURE 8
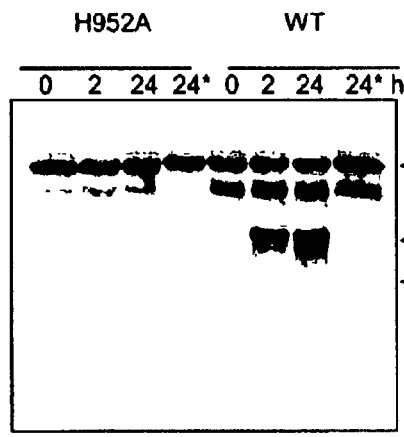
A. anti-NS3
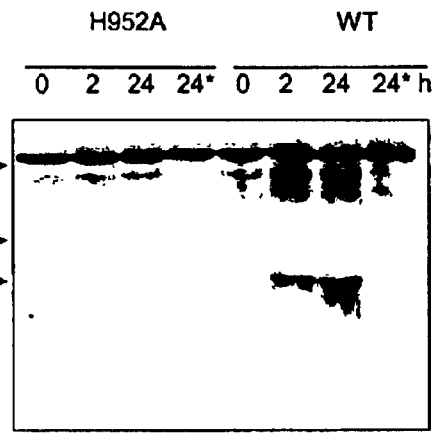
B. anti-His6

FIGURE 9A

NUCLEOTIDE SEQUENCE OF 4K-6H-NS2/3 (904-1206) ST-4K (SEQ ID NO. 3)

```
atgaaaaaga aaaagctcga gcatcaccat caccatcaca ctagtgcagg cataaccaaa
gtgccgtact tcgtgcgtgc gcaggggctc attcgtgcgt gtatgttggt gcggaaggct
gcggggggtc attatgtcca aatggccttc atgaagctag ctgcgctgac aggtacgtac
gtttatgacc atctcactcc attgcaggat tgggcccacg cgggcctacg agaccttgca
gtggcggtag agcccgtcat cttctctgac atggaggtca agatcatcac ctgggggggcg
gacaccgcgg catgcgggga catcatttca ggtctgcccg tctccgctcg aaggggaagg
gagatactcc tgggaccggc cgataatttt gaagggcagg ggtggcgact ccttgcgccc
atcacggcct actcccaaca gacacggggc ctacttggtt gcatcatcac cagcctcaca
ggccgggaca agaaccaggt cgaggggag gttcaagtgg tctccaccgc tacacaatct
ttcctggcga cctgcgtcaa cggcgtgtgt tggactgtct tccatggcgc cggctcaaag
accttggccg gccccaaagg cccaatcacc cagatgtaca ctaatgtgga ccaggacctc
gtcggctggc aggcgccccc tggggcgcgc tccatgacac catgcacctg cggcagctcg
gacctctatt tggtcacgag acatgccgac gtcattccgg tgcgccggcg gggcgacagt
agggggagcc tgctctcccc caggcctgtc tcctacttga agggctcttc gggtggccca
ctgctctgcc cttcggggca cgttgtgggc atcttccggg ctgctgtgtg cacccggggg
gttgcaaaag cggtggactt catacctgtt gagtctatgg aaactaccat gcggactagt
agcgcttggc gtcacccgca gttcggtggt aaaaagaaaa agtaaggatc c
```

FIGURE 9B

AMINO ACID SEQUENCE OF 4K-6H-NS2/3 (904-1206) ST-4K (SEQ ID NO. 4)

```
MKKKKLEHHH HHHTSAGITK VPYFVRAQGL IRACMLVRKA AGGHYVQMAF MKLAALTGTY    60
VYDHLTPLQD WAHAGLRDLA VAVEPVIPSD MEVKIITWGA DTAACGDIIS GLPVSARRGR   120
EILLGPADNF EGQGWRLLAP ITAYSQQTRG LLGCIITSLT GRDKNQVEGE VQVVSTATQS   180
FLATCVNGVC WTVFHGAGSK TLAGPKGPIT QMYTNVDQDL VGWQAPPGAR SMTPCTCGSS   240
DLYLVTRHAD VIPVRRRGDS RGSLLSPRPV SYLKGSSGGP LLCPSGHAVG IFRAAVCTRG   300
VAKAVDFIPV ESMETTMRTS SAWRHPQFGG KKKK                               337
```

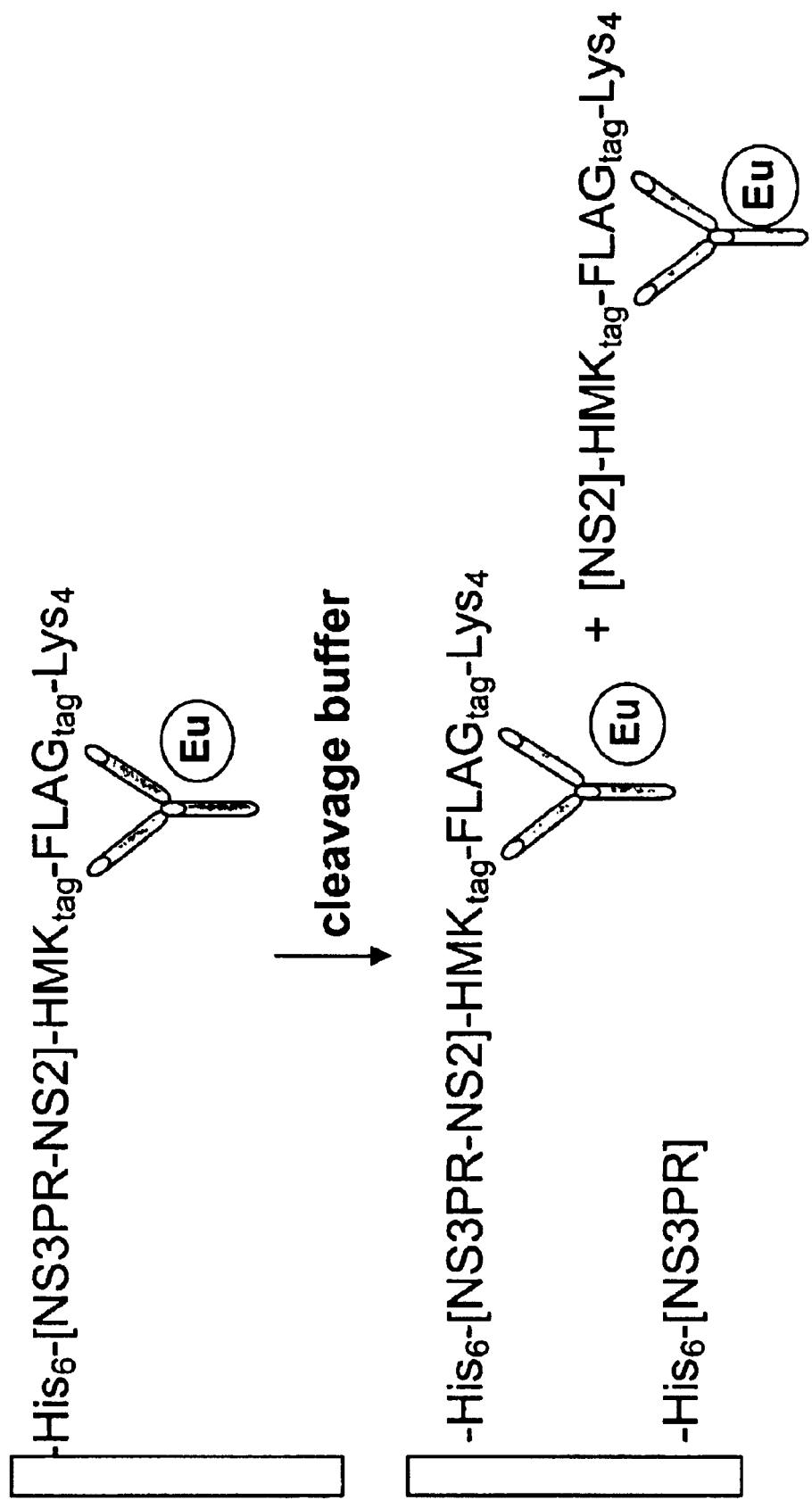

PURIFIED ACTIVE HCV NS2/3 PROTEASE

RELATED APPLICATIONS

This application claims benefit of U.S. Provisional Application Ser. No. 60/256,031, filed on Dec. 15, 2000.

FIELD OF THE INVENTION

The invention relates generally to purification and activation methods for Hepatitis C virus (HCV) NS2/3 protease, particularly to a method of producing a refolded, inactive NS2/3 protease or truncations thereof which can later be activated for auto-cleavage. More particularly, the method provides for truncated, purified active HCV NS2/3 protease and assays for identifying inhibitors thereof.

BACKGROUND OF THE INVENTION

Hepatitis C Virus (HCV) is an important cause of chronic liver disease leading to cirrhosis and end-stage liver disease in humans. Over 150 million people worldwide are persistently infected with HCV and the number of deaths attributable to chronic infection is likely to rise dramatically over the next 10–20 years. Currently available therapies are of limited efficacy and are unsatisfactory. These therapies have involved use of interferon alpha, either alone or in combination with other antiviral agents such as ribavirin. Given that a low response rate, in addition to high patient relapse and side effects, are observed, new therapies are required that may afford long-term treatment benefits.

The cloned and characterized partial and complete sequences of the HCV genome have been analyzed to provide appropriate targets for prospective antiviral therapy. HCV is an enveloped positive strand RNA virus in the Flaviviridae family. The single strand HCV RNA genome is approximately 9600 nucleotides in length and has a single open reading frame (ORF) encoding a single large polyprotein of about 3010 amino acids. In infected cells, this polyprotein is cleaved at multiple sites by cellular and viral proteases to produce the structural and non-structural (NS) proteins. In the case of HCV, the generation of mature nonstructural proteins (NS2, NS3, NS4A, NS4B, NS5A, and NS5B) is effected by two viral proteases. The first one, as yet poorly characterized, cleaves at the NS2/3 junction and is henceforth referred to as NS2/3 protease. The second one is a serine protease contained within the N-terminal region of NS3, henceforth referred to as NS3 protease, and mediates all the subsequent cleavages downstream of NS3, both in cis, at the NS3/4 A cleavage site, and in trans, for the remaining NS4A/4B, NS4B/5A, NS5A/5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B is a RNA-dependent RNA polymerase that is involved in the replication of HCV.

Most of the HCV encoded enzymes have been evaluated as targets for the development of new antiviral therapies, namely the NS3 protease, helicase and ATPase activities, as well as the NS5B RNA-dependent RNA polymerase activity (Dymock, B. W. et al. (2000) *Antiviral Chemistry & Chemotherapy.* 11 (2):79–96 and Walker, M. A. (1999) *Drug Discovery Today* 4(11): 518–529). The only viral enzyme that has not been extensively characterized so far is the NS2/3 protease, probably because it acts co-translationally.

NS2/3 protease is responsible for autocleavage at the NS2 and NS3 junction between amino acids Leu1026 and Ala1027 (Hirowatari, Y., et al (1993) *Arch. Virol.* 133:349–356 and Reed, K. E., et al. (1995) *J. Virol.* 69 (7) 4127–4136). This cleavage appears to be essential for productive replication in vivo as shown by the absence of HCV infection in a chimpanzee following inoculation with a clone devoid of the NS2/3 protease activity (Kolykhalov, A. A., et al (2000) *J. Virol.* 74 (4) 2046–2051). It also appears that generation of a functional NS2 and an authentic NS3 protease N-terminal sequence are somehow linked to NS5A phosphorylation (Liu, Q., et al. (1999) *Biochem. Biophys. Res. Commun.* 254, 572–577 and Neddermann P., et al. (1999) *J. Virol.* 73(12):9984–9991).

The minimal region of the HCV open reading frame required for the autocleavage activity has been reported to be located somewhere between amino acids 898 and 907 for the N-terminal boundary and amino acid 1206 for the C-terminal boundary (Hijikata, M. et al (1993) *J. Virol.* 67 (8):4665–4675.; Grakoui, A., et al. (1993) *Proc. Natl. Acad. Sci. USA* 90:10583–10587; Santolini, E., et al (1995) *J. Virol.* 69 (12): 7461–7471; and Liu, Q., et al (1999) *Biochem. Biophys. Res. Commun.* 254, 572–577; Pallaoro et al., (2001) *J. Virol.* 75(20); 9939–46). Interestingly, the NS2/3 protease activity is independent of the NS3 protease activity (Grakoui, A., et al. (1993) *Proc. Natl. Acad. Sci. USA* 90:10583–10587; Hijikata, M. et al (1993) *J. Virol.* 67 (8):4665–4675) but the NS3 protease domain cannot be substituted by another non-structural protein (Santolini, E., et al (1995) *J. Virol.* 69 (12): 7461–7471). Mutagenesis studies have shown that the residues His952 and Cys993 are essential for the cis-cleavage activity (Grakoui, A., et al. (1993) *Proc. Natl. Acad. Sci. USA* 90:10583–10587; Hijikata, M. et al (1993) *J. Virol.* 67 (8):4665–4675). Gorbalenya, A. E, et al. (1996) *Perspect. Drug Discovery Design.* 6:64–86)) have suggested that the NS2/3 protease could be a cysteine protease. However, the observation that the activity is stimulated by metal ions and inhibited by EDTA led to the suggestion that the NS2/3 protease is a metalloprotease (Grakoui, A., et al. (1993) *Proc. Nat. Acad. Sci. USA* 90:10583–10587; Hijikata, M. et al (1993)*J. Virol.* 67 (8):4665–4675)). Studies with classical protease inhibitors in an in vitro transcription and translation assay (Pieroni, L. et al (1997)*J. Virol.* 71 (9): 6373–6380) have not yet allowed for a definitive classification.

Processing at the NS2/3 junction has been reported (Darke, P. L. et al (1999) *J. Biol. Chem.* 274 (49) 34511–34514 and WO 01/16379; Grakoui, A., et al (1993). *Proc. Natl. Acad. Sci. USA* 90:10583–10587; Hijikata, M., et al. (1993) *J. Virol.* 67 (8):4665–4675; Pieroni, L., et al (1997) *J. Virol.* 71 (9): 6373–6380 and Santolini, E. et al (1995)*J. Virol.* 69 (12): 7461–7471) following expression of the NS2/3 region in cell-free translation systems, in *E. coli*, in insect cells infected with baculovirus recombinants and/or in mammalian cells (transient transfection or vaccinia virus T7 hybrid system). However, processing has not been reported in an isolated recombinant enzyme until very recently (Pallaoro et al., (2001) *J. Virol.* 75(20); 9939–46; Thibeault et al., J. Biol. Chem. 276 (49):46678–46684).

Grakoui et al. (1993) *Proc. Natl. Acad. Sci. USA,* 90:10583–10587 and Komoda et al. (1994) *Gene,* 145:221–226 have both disclosed the expression of HCV polypeptides, including the NS2/3 protease, in *E. coli*. Following expression, processing was assessed from SDS-PAGE and immunoblot analyses of cell lysates.

Komoda, using HCV polyproteins fused to maltose-binding protein (MBP) at their N-terminus and dihydrofolate reductase (DHFR) at their C-terminus, also reported on the partial purification of the DHFR-fused products from cell lysates by affinity chromatography for N-terminal sequencing purpose only.

Thus, the biochemical characterization of the NS2/3 protease as well as mechanistic and structural studies has been hampered due to the unavailability of a pure recombinant form of the enzyme. Before any potential inhibitors of NS2/3 protease can be identified in a high throughput-screening format, there must be a reliable source of purified, active NS2/3 protease.

WO 01/68818 published on Sep. 20, 2001 {as well as Pallaoro et al., (2001) J. Virol. 75(20); 9939–46} have described a process for the purification of recombinant active NS2/3 protease. However, their refolding method needs to be carried out at 4° C. to avoid auto-catalysis.

The method of the present invention, also disclosed in Thibeault et al., J. Biol. Chem. 276 (49):46678–46684, discloses a purification method that proceeds in 2 steps, can be carried out at room temperature and leads in the first instance to a soluble inactive NS2/3 protease (stable at RT) that can be scaled up and stored safely without auto-cleavage.

It is therefore an advantage of this invention to provide a method for the purification of refolded inactive NS2/3 protease.

It is a further advantage of this invention that the soluble inactive protease can be further activated to produce soluble active NS2/3 protease for large scale screening efforts.

It is also a further advantage of this invention to provide a purified recombinant active NS2/3 protease and truncations thereof in such scale that small molecules and ligands can be screened as potential inhibitors.

The present description refers to a number of documents, the content of which is herein incorporated by reference.

SUMMARY OF THE INVENTION

The present invention reduces the difficulties and disadvantages of the prior art by providing a novel method for purifying and activating HCV NS2/3 protease. Advantageously, this method both solubilizes the protease and refolds it under conditions that will not promote auto-cleavage of the protease. Moreover, the method has a further advantage in that a N-terminal truncated form of NS2/3 protease is produced at high levels in inclusion bodies using recombinant methods following its expression in *E. coli*. This high level production allows for large amounts of the protease to be isolated and purified.

This is the first report of an isolated, inactive NS2/3 protease that is stable at room temperature without proceeding to auto-catalysis. It is also the first report of a purified recombinant active NS2/3 protease obtained from the method of the invention. The availability of the purified recombinant NS2/3 protease will allow for a detailed biochemical characterization of the enzyme and the development of in vitro assays for screening novel inhibitors.

According to a first embodiment, the invention provides a method of producing a refolded, inactive HCV NS2/3 protease, comprising the steps of:
  a) isolating the protease in the presence of a chaotropic agent;
  b) refolding the isolated protease by contacting it with a reducing agent and lauryldiethylamine oxide (LDAO) in the presence of reduced concentration of chaotropic agent or polar additive.

In accordance with a second embodiment of this invention, there is provided a method for producing an active NS2/3 protease comprising:
  c) adding an activation agent to a medium containing soluble inactive NS2/3 protease obtained in step b), thereby forming a cleavage/activation buffer so as to induce auto-cleavage of the NS2/3 protease.

In a third embodiment, the invention provides a method of assaying the activity of NS2/3 protease comprising:
  d) incubating the NS2/3 protease in the cleavage/activation buffer of step c) for sufficient time so that the NS2/3 protease autocleaves; and
  e) measuring the presence or absence of cleavage products, or fragments thereof, as an indication of the autocleavage.

In accordance with a fourth embodiment of the invention, there is provided an assay for screening a candidate drug or ligand that inhibits the protease activity of a NS2/3 protease comprising:
  d) incubating a sample of the NS2/3 protease in the cleavage/activation buffer of step c) for sufficient time in the presence of, or absence of the candidate drug or ligand;
  e) measuring the amount of cleavage products or fragments thereof; and
  f) comparing the amount of the cleavage products or the fragments thereof, in the presence of, or absence of the candidate drug or ligand.

In accordance with a fifth embodiment of the invention, there is provided a refolded inactive NS2/3 protease, a truncation or a functionally equivalent variant thereof, having the minimal amino acid sequence from residues 906 to 1206 of the full-length NS2/3 protease as numbered according to the numbering used in FIG. 1B.

In accordance with a sixth embodiment of the invention, there is provided a composition comprising an isolated NS2/3 protease selected from full length NS2/3 protease, a truncation thereof or a sequence as defined according to SEQ ID NO: 2, 4, 10, 11, 12, 13, 14 and 15, wherein said protease is in a solution comprising a sufficient concentration of LDAO to prevent auto-cleavage of said protease.

BRIEF DESCRIPTION OF THE DRAWINGS

Having thus generally described the invention, reference will now be made to the accompanying drawings, showing by way of illustration a preferred embodiment thereof, and in which:

FIG. 1A shows a nucleotide sequence of full length NS2/3 (810-1206)st (SEQ ID NO: 1) of HCV 1*b* genotype.

FIG. 1B shows an amino acid sequence of the full length NS2/3 (810-1206)st (SEQ ID NO: 2) encoded by the nucleotide sequence of FIG. 1A.

FIG. 2 shows an N-terminal truncation study in which HCV NS2/3 protease full-length and N-terminal deletion mutants encompassing amino acids from 815-915 to 1206 were cloned in the pET11 d expression vector. NS2/3 protease constructs were translated in vitro with a rabbit reticulocyte lysate. Translated [$^{35}$S]-labeled products were separated by SDS-PAGE (15%) and visualized with a Phosphorlmager (A). *E. coli* expression of the NS2/3 protease constructs without induction (lanes −) or following a 2 h-induction at 37° C. with 1 mM IPTG (lanes +) was evaluated by SDS-PAGE (15%) (B) and immunoblot analysis using an anti-NS3 polyclonal antibody (C). Lanes are numbered according to the first amino acid of the NS2/3 protease expressed in each transcript. The positions of the molecular mass standards are indicated as well as the NS3 protease.

Figure 3:
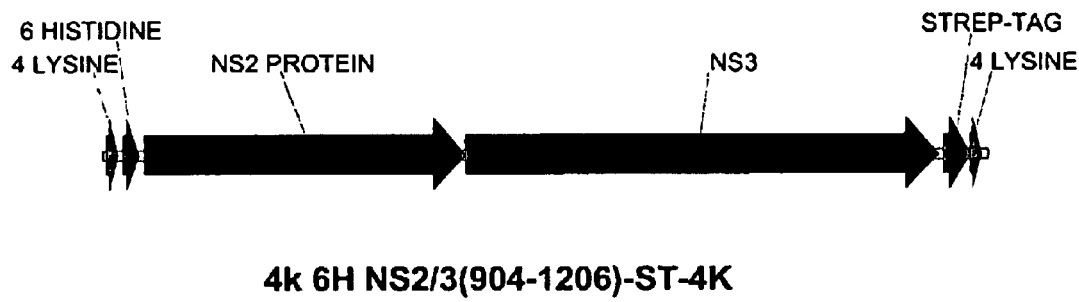

FIG. 3 shows a diagram representing an HCV NS2/3 protease construct that encompasses amino acid residues 904-1206, along with N- and C-terminal lysine residues, an N-terminal hexahistidine tag and a C-terminal streptavidin tag ("st").

Figure 4:
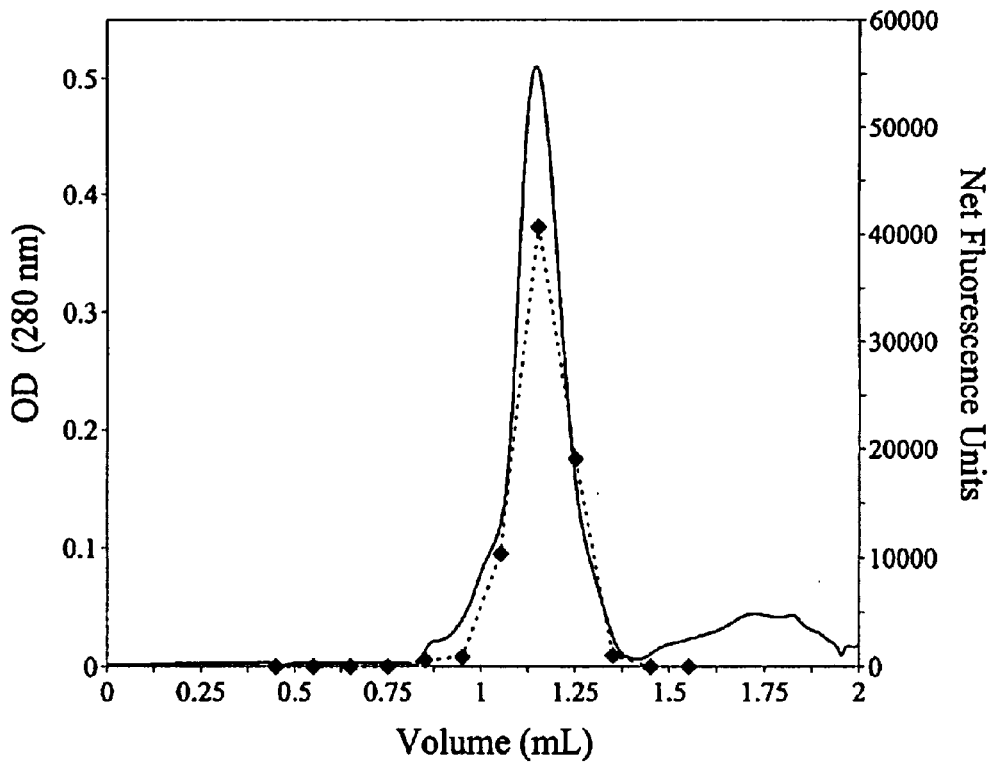

FIG. 4 shows a chromatogram obtained from the refolding 4K-6H—NS2/3 (904-1206)st-4K (SEQ ID NO: 4) on Superose 12 gel filtration column. Following the addition of 5 mM TCEP and 5 mM $ZnCl_2$ to the purified inclusion bodies, the enzyme was refolded and eluted in Tris 50 mM, pH 8.0, 0.5 M arginine-HCl, 1% LDAO, 5 mM TCEP. Solid line (—) represents absorbance at 280 nm and dotted line (-----♦----) indicates NS3 protease domain activity monitored on selected fractions using the fluorogenic substrate anthranilyl-DDIVPAbu[C(O)—O] AMY(3-$NO_2$)TW—OH.

Figure 5:
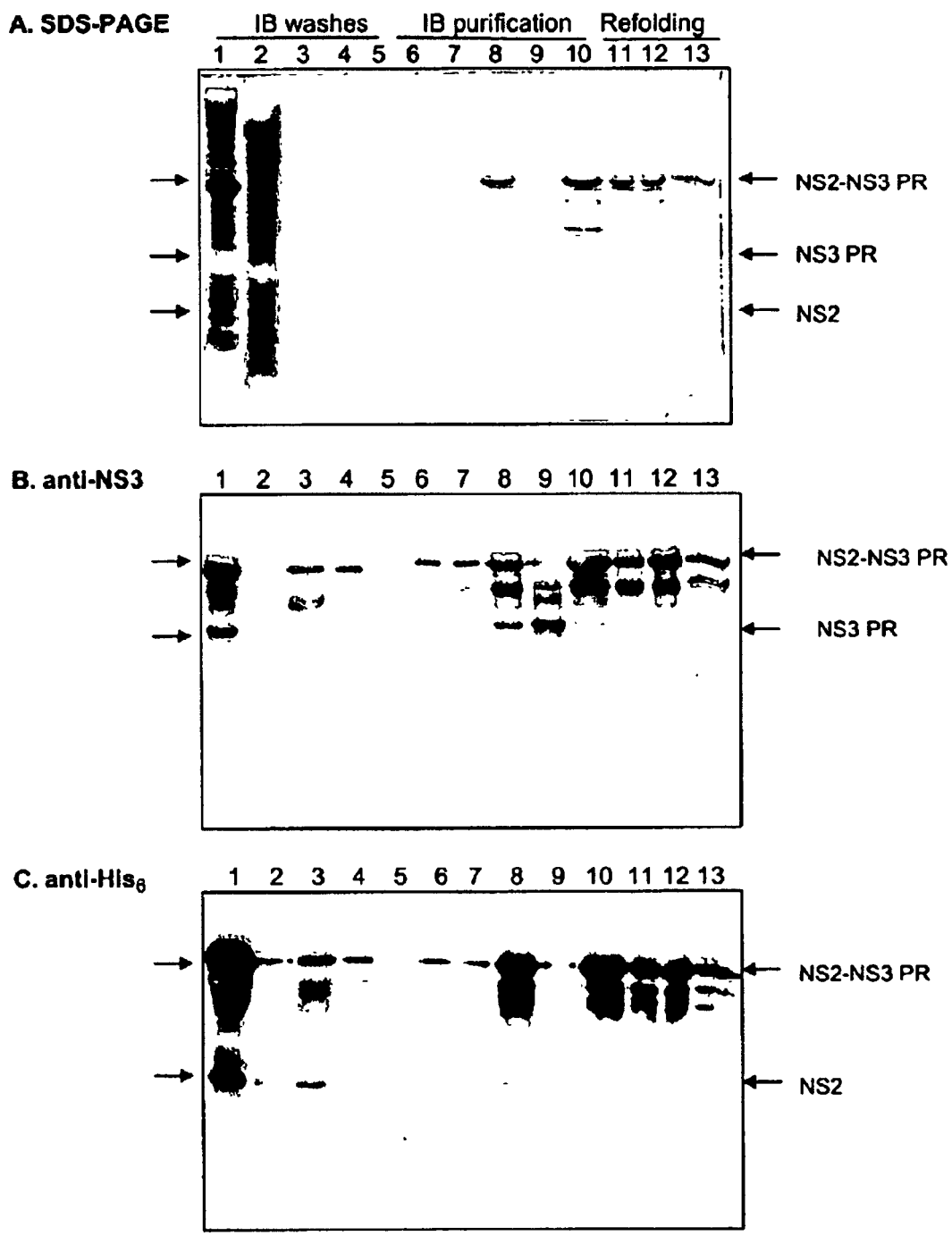

FIG. 5 shows the production and purification of 4K-6H—NS2/3 (904-1206)st-4K from inclusion bodies monitored by 15% SDS-PAGE stained with Coomassie blue (A) immunoblot analysis using an anti-NS3 rabbit antisera (B) and immunoblot analysis using an anti-$His_6$ rabbit antisera (C). Lane 1: crude E. coli cell extract; lanes 2–5: inclusion bodies (IB) washes; lanes 6–10: inclusion bodies purification on $Ni^{2+}$-chelating column; lane 11: purified inclusion bodies; lane 12: load of Superose 12 gel filtration column; lane 13: refolded enzyme (see Examples for details). The unprocessed enzyme and the cleavage products 4K-6H—NS2 (904-1026) and NS3 (1027-1206)st-4K are indicated.

Figure 6:
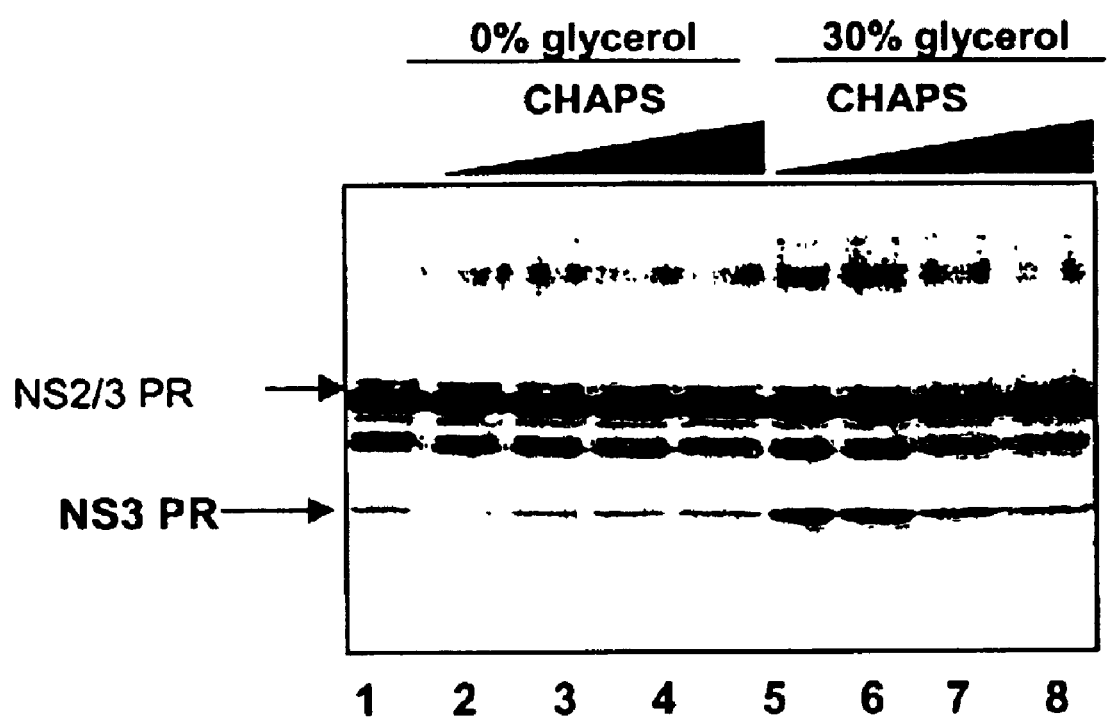

FIG. 6 shows the effect of glycerol and CHAPS on the autoprocessing activity of the 4K-6H—NS2/3 (904-1206) st-4K monitored by immunoblot using an anti-NS3 rabbit antisera. The autocleavage reaction was initiated by dilution of the refolded enzyme in 50 mM Tris, pH 8.0, 1 mM TCEP containing various amount of glycerol and CHAPS followed by an incubation of 18 h at 23° C. Lane 1: 30% glycerol, no CHAPS; lanes 2–5: no glycerol and 0.1, 0.25, 0.5 or 1.0% CHAPS respectively; lanes 6–9: 30% glycerol and 0.1, 0.25, 0.5 and 1.0% CHAPS respectively. The unprocessed enzyme and the NS3 (1027-1206)st-4K product are indicated.

FIG. 7 shows a time-course of 4K-6H—NS2/3 (904-1206)st-4K cis-cleavage monitored by immunoblot using anti-NS3 rabbit antisera (A) and anti-$His_6$ rabbit antisera (B). The autocleavage reaction was initiated by diluting the refolded enzyme in 50 mM Hepes, pH 7.0, 50% glycerol (w/v), 1% n-β-D-dodecyl maltoside, 1 mM TCEP and incubating for 0, 1, 2, 4, 6 and 24 h at 23° C. The unprocessed enzyme and the products 4K-6H—NS2 (904-1026) and NS3 (1027-1206)st-4K are indicated.

FIG. 8 shows a comparison of the NS2—NS3 protease activity of the purified His952Ala ("H952A") mutant (SEQ ID NO: 16) of 4K-6H—NS2/3 (904-1206)st-4K and the purified WT by immunoblot analyses using an anti-NS3 antisera (A) or an anti-$His_6$ antisera (B). The autocleavage reaction was performed in 50 mM Hepes, pH 7.0, 50% glycerol (w/v),1% n-β-D-dodecyl-maltoside, 1 mM TCEP for 0, 2 and 24 h at 23° C. A 24 h-incubation was also performed in the absence of detergent (lane 24*). The unprocessed enzyme and the autocleavage products 4K-6H—NS2 (904-1026) and NS3 (1027-1206)st-4K are indicated.

FIG. 9A shows a nucleotide sequence of 4K-6H—NS2/3 (904-1206)st-4K (SEQ ID NO: 3).

FIG. 9B shows an amino acid sequence of 4K-6H—NS2/3 (904-1206)st-4K (SEQ ID NO: 4) encoded by the nucleotide sequence of FIG. 9A.

FIG. 10 is a diagram illustrating the format of a Heterogeneous Time-Resolved Fluorescence (TRF) Assay.

Figure 11:
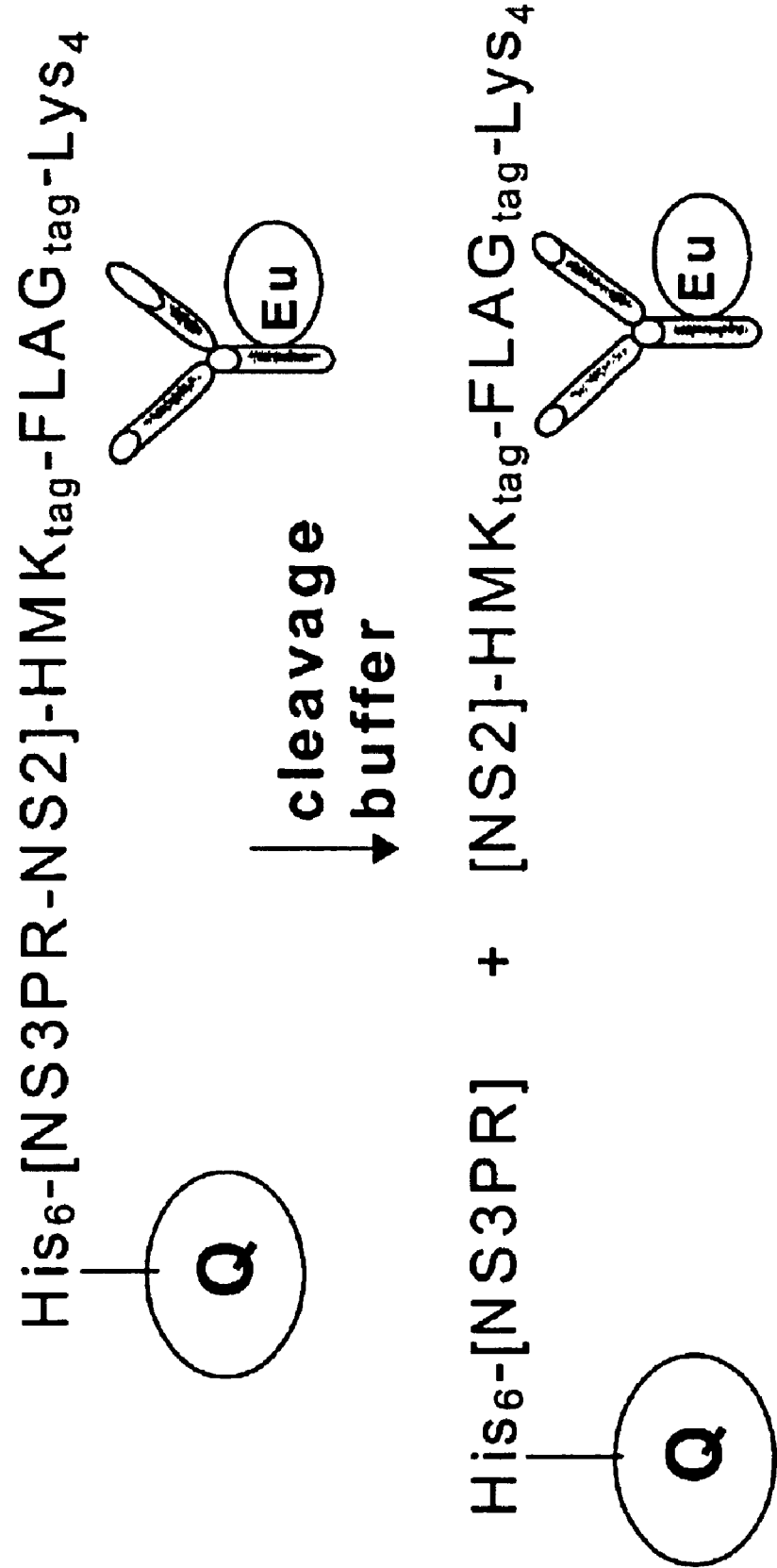

FIG. 11 is a diagram illustrating the format of a Homogeneous Time-Resolved Fluorescence (TRF) Assay.

Figure 12:
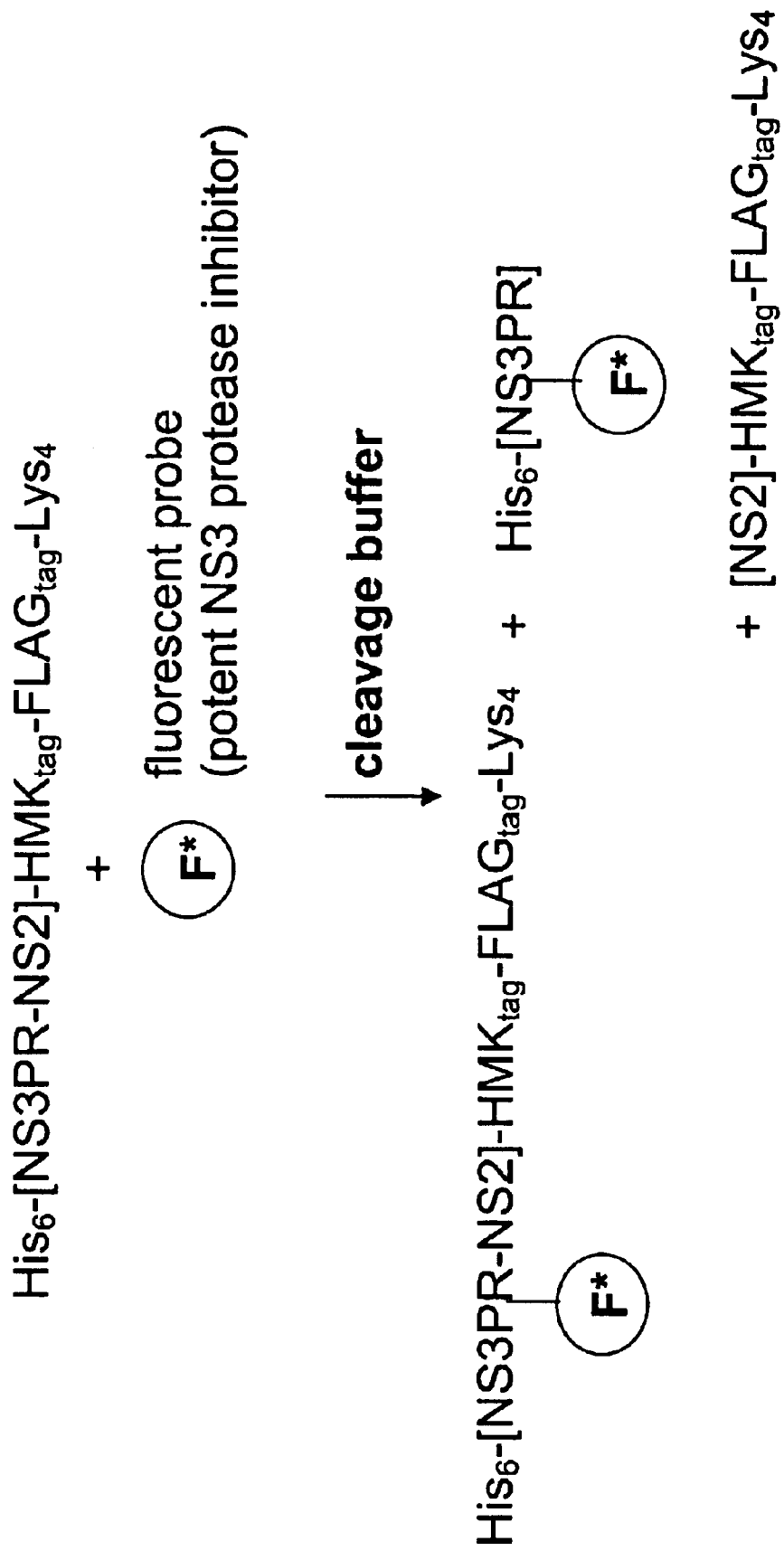

FIG. 12 is a diagram illustrating the format of a Fluorescence Polarization Assay.

Figure 13:

FIG. 13 is a diagram illustrating the format of a Radiometric Assay.

Figure 14:
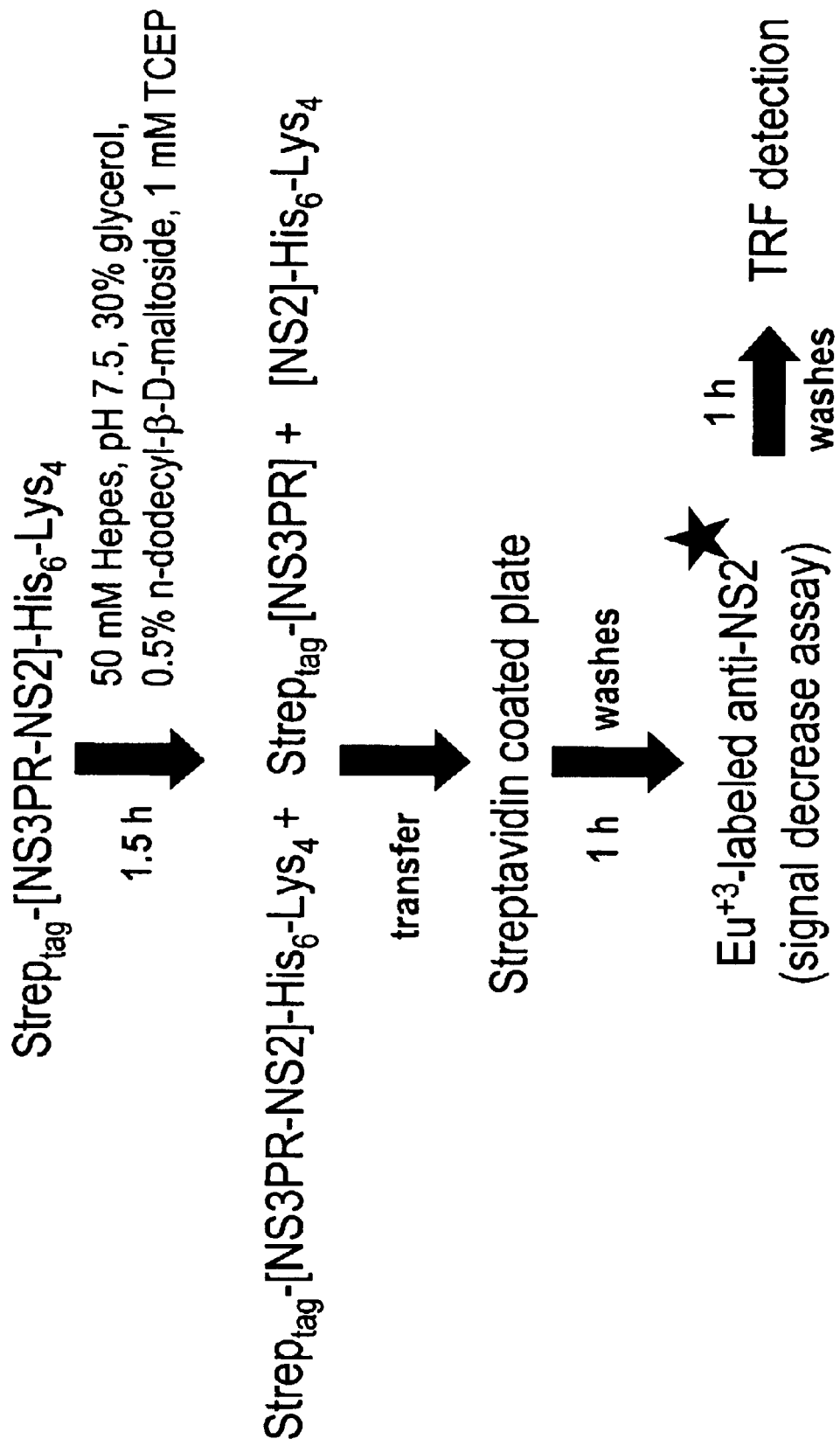

FIG. 14 is a schematic representation of an alternative TRF assay format using the purified NS2/3 protease of the invention.

DETAILED DESCRIPTION OF PREFERRED EMBODIMENTS

Definitions

Unless otherwise defined, all technical and scientific terms used herein have the same meaning as those commonly understood by one of ordinary skill in the art to which the invention pertains. Generally, the procedures for cell culture, infection, molecular biology methods and the like are common methods used in the art. Such techniques can be found in reference manuals such as, for example, Sambrook et al. (1989, Molecular Cloning—A Laboratory Manual, Cold Spring Harbor Laboratories) and Ausubel et al. (1994, Current Protocols in Molecular Biology, Wiley, N.Y.).

Nucleotide sequences are presented herein by single strand, in the 5' to 3' direction, from left to right, using the one letter nucleotide symbols as commonly used in the art and in accordance with the recommendations of the IUPAC-IUB Biochemical Nomenclature Commission (Biochemistry, 1972, 11:1726–1732).

As used herein, the terms "NS2/3 protease", "protease" and "enzyme" are used interchangeably throughout this specification and refer to an HCV encoded NS2/3 protease.

As used herein, the term "active NS2/3 protease" is intended to describe NS2/3 protease that retains a detectable level of cleavage activity between residues 1026–1027. The protease activity is measured by monitoring the levels of remaining uncleaved NS2/3 protease, cleavage products such as either NS2 protein or NS3 protease, or a fragment thereof, for example, in enzymatic assays, ELISA or by Western blot analysis.

As used herein, the term "isolated", when referring to NS2/3 protease, is intended to mean that the NS2/3 protease is enriched with respect to cellular components. Particularly, this term means that the NS2/3 protease is enriched 50% or greater when compared to contaminating cellular components.

As used herein, the term "purifying" or "purified", when referring to NS2/3 protease, is intended to mean that the NS2/3 protease is substantially free of contaminating cellular components. Preferably, the NS2/3 protease is purified to a purity of about 90%. More preferably, the NS2/3 protease is purified to about 95%. Most preferably the NS2/3 protease is purified to a purity of about 98%.

As used herein, the term "inactive NS2/3 protease" is intended to describe NS2/3 protease that has significantly reduced, or essentially eliminated, cleavage activity between residues Leu1026-Ala1027, as determined by SDS-PAGE.

As used herein, the term "nucleic acid molecule" is intended to include DNA molecules (e.g., cDNA or genomic DNA) and RNA molecules (e.g., mRNA). The nucleic acid molecule may be single-stranded or double-stranded, but preferably is double-stranded DNA.

As used herein, the term "vector" refers to a nucleic acid molecule capable of transporting another nucleic acid molecule to which it has been linked. One type of vector is a "plasmid", which refers to a circular, double-stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" may be used interchangeably, as the plasmid is the most commonly used form of vector. However, the invention is intended to include such other forms of expression vectors, such as viral vectors, which serve equivalent functions.

As used herein, the term "host cell" is intended to refer to a cell into which a nucleic acid of the invention, such as a recombinant expression vector of the invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may be, in fact, non-identical to the parent cell, but are still included within the scope of the term as used herein.

As used herein, the term "recombinant" or "recombinantly produced" is intended to indicate that a cell replicates or expresses a nucleic acid molecule, or expresses a peptide or protein encoded by a nucleic acid molecule whose origin is exogenous to the cell. In particular the recombinant cell can express genes that are not found within the native (non-recombinant) form of the cell.

As used herein, a "functionally equivalent variant", when used to describe the NS2/3 protease, is intended to refer to a protein sequence where one or more amino acids are replaced by other amino acid(s) or unnatural amino acid(s) that do not substantially affect the NS2/3 protease activity. Such replacements include conservative amino acid substitutions or degenerate nucleic acid substitutions. When relating to a protein sequence, the substituting amino acid has chemico-physical properties which usually, but not necessarily, are similar to that of the substituted amino acid. The similar chemico-physical properties include, similarities in charge, bulkiness, hydrophobicity, hydrophilicity and the like. Some of the most commonly known conservative amino acid substitutions include, but are not limited to: Leu or Val or Ile; Gly or Ala; Asp or Glu; Asp or Asn or His; Glu or Gln; Lys or Arg; Phe or Trp or Tyr; Val or Ala; Cys or Ser; Thr or Ser; and Met or Leu.

As used herein, the term "inhibit", when used in reference to the NS2/3 protease, is intended to mean that the protease's ability to autocleave is decreased. Drugs or ligands that can inhibit NS2/3 protease (hereinafter referred to as "potential inhibitors") may be useful for modulating HCV infection in a population of cells and, therefore, may be useful as medicaments for treating a pathology characterized by the presence of HCV in the cells.

As used herein, the term "refolded", when used in reference to the NS2/3 protease, is intended to refer to the process by which the unfolded, or improperly folded, NS2/3 protease undergoes conformational changes (partial or complete) so as to attain a conformation that is soluble and stable without detectable autocleavage activity at room temperature. The refolded protease requires addition of an activation detergent to become activated.

As used herein, the term "autocleavage" or "autocleaved", when used to describe NS2/3 protease, is intended to mean that the cleavage at the NS2/3 junction (Leu1026-Ala1027) occurs intramolecularly without an exogenous substrate.

The term "affinity label" or "affinity tag" as used herein refers to a label which is specifically trapped by a complementary ligand. Examples of pairs of affinity marker/affinity ligand include but are not limited to: Maltose-Binding Protein (MBP)/maltose; Glutathione S Transferase (GST)/glutathione; histidine (His)/metal; streptavidin tag/streptavidin or neutravidin. The metal used as affinity ligand may be selected from the group consisting of: cobalt, zinc, copper, iron, and nickel (Wong et al. (1991) Separation and Purification Methods, 20(1), 49–106). The affinity label may be positioned on the N- or C-terminal end of the protein, but preferably on the N-terminus of the protein. Preferably, the metal selected is nickel. The affinity ligand can be set up in columns to facilitate separation by affinity chromatography.

PREFERRED EMBODIMENTS

I. Method of Refolding and Purification

According to a first aspect of the first embodiment of the present invention, there is provided a method of producing a refolded, inactive HCV NS2/3 protease, comprising the steps of:

a) isolating the protease from inclusion bodies in the presence of high concentration of a chaotropic agent;

b) refolding the isolated protease by contacting the protease with a reducing agent and LDAO in the presence of low concentration of chaotropic agent or polar additive.

In a preferred aspect of the first embodiment, the active NS2/3 protease is produced using recombinant DNA techniques. The expression vectors of the invention (see Examples) comprise a nucleic acid of the invention in a form suitable for expression of the protein in a host cell, which means that the recombinant expression vectors include one or more regulatory sequences, selected on the basis of the host cells to be used for expression, which is operatively linked to the nucleic acid sequence coding for the protein to be expressed. Within a recombinant expression vector, "operably linked" is intended to mean that the nucleotide sequence of interest is linked to the regulatory sequence(s) in a manner which allows for expression of the corresponding amino acid sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector may depend on such factors as the choice of the host cell to be transformed, the level of expression of protein desired, etc. The expression vectors of the invention can be introduced into host cells to thereby produce proteins or peptides encoded by nucleic acids as described herein (e.g. NS2/3 protease, truncations or mutant forms of NS2/3 protease).

The recombinant expression vectors of the invention can be designed for expression of NS2/3 protease in prokaryotic or eukaryotic cells. For example, NS2/3 protease can be expressed in bacterial cells such as E. coli, insect cells (using baculovirus expression vectors), yeast cells or mammalian cells. Suitable host cells are discussed further in Goeddel, Gene Expression Technology: Methods in Enzymology 185, Academic Press, San Diego, Calif. (1990).

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification (e.g. affinity tag such as a hexahistidine tag). One strategy to maximize recombinant protein expression in E. coli is to express the protein in a host bacteria with an impaired capacity to proteolytically cleave the recombinant protein (Gottesman, S., Gene Expression Technology: Methods in Enzymology 185, Academic Press, San Diego, Calif. (1990) 119–128). Another strategy is to alter the nucleic acid sequence of the nucleic acid to be inserted into an expression vector so that the individual codons for each amino acid are those preferentially utilized in E. coli (Wada et al., (1992) Nuc. Acids Res. 20:2111–2118). Such alteration of nucleic acid sequences of the invention can be carried out by standard DNA synthesis techniques.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (Molecular Cloning: A Laboratory Manual, 2nd Edition, Cold Spring Harbor Laboratory press (1989)), and other laboratory manuals.

Often during protein expression, so-called inclusion bodies are formed. The NS2/3 protease may be isolated from the host cell, e.g. by lysing the host cell and recovering the recombinant NS2/3 protease from the inclusion bodies. Inclusion bodies are aggregates of intact proteins or polypeptides in non-native-like conformations (see Current Protocols in Protein Science (1997) John Wiley & Sons Inc.). There are many examples of how to extract protein from inclusion bodies and these are discussed in Current Protocols in Protein Science. The host cell of the invention, such as a prokaryotic or eukaryotic host cell in culture, can be used to produce NS2/3 protease of the present invention.

Accordingly, the invention further includes culturing a host cell in a culture medium. The host cell contains an expression vector that has a coding region of a nucleic acid sequence that encodes NS2/3 protease, resulting in the production of unfolded or improperly folded inactive recombinant NS2/3 protease in inclusion bodies. The host cells are lysed with a lysis buffer to produce host cell lysates. The inclusion bodies in the host cell lysates are recovered therefrom by low speed centrifugation. Preferably, the lysis buffer contains about 0.1% Triton X-100. The inclusion bodies are then selectively extracted using an extraction buffer that preferably contains about 2% Triton X-100 and 2 M urea. Preferably, both the lysis buffer and the extraction buffer contain a reducing agent selected from the group consisting of DTT and TCEP.

In another aspect of the first embodiment, the inclusion bodies, containing inactive NS2/3 protease, are then isolated by low speed centrifugation following selective extraction from pellets obtained from the low speed centrifugation from the host cell lysates described above. The isolated inclusion bodies are treated with a chaotropic agent at a sufficient concentration to produce soluble inactive NS2/3 protease. Preferably, the chaotropic reagent is selected from the group consisting of guanidine, guanidine-HCl and urea. More preferably, the chaotropic agent is guanidine-HCl. Preferably, the sufficient concentration is between 4 M and 9 M. More preferably, guanidine or guanidine-HCl is at a concentration between 4 and 8 M; most preferably at 6 M. Preferably, urea is at a concentration between 6 and 9 M; more preferably 8 M.

Alternatively, recombinant NS2/3 protease may also be prepared as an extracellular protein by operatively linking a heterologous signal sequence to the amino-terminus of the protease such that it is secreted from a eukaryotic cell. In this case, recombinant NS2/3 protease can be recovered from the culture medium in which the cells are cultured.

In another aspect of the first embodiment, the NS2/3 protease in constructed to contain an affinity-tag that can be used such that the soluble inactive NS2/3 protease can be isolated from the inclusion bodies using affinity chromatography. Such affinity tag and corresponding ligand are well known in the art.

In a preferred aspect of the first embodiment, LDAO is used at or above its critical micelle concentration. More preferably, LDAO is at a concentration between 0.003% and 1%. In a most preferred aspect, LDAO is used at a concentration between 0.03% and 1%. Without intending to be bound by theory, the inventors believe that LDAO present in the refolding (gel filtration) buffer is required for refolding but not sufficient for cis-cleavage of the enzyme.

In a preferred aspect of the first embodiment step b), the chaotropic agent or polar additive is selected from the group consisting of: guanidine, guanidine hydrochloride, urea and arginine-hydrochloride. More preferably, guanidine-hydrochloride or arginine-HCl is used. Most preferably, arginine-HCl is used.

In a preferred aspect of the first embodiment step b) the chaotropic agent or polar additive is preferably used at a concentration between 0.25 M and 2 M. In a most preferred aspect, it is used at a concentration between 0.5 M and 1 M, most preferably, at a final concentration of 0.5 M.

In another preferred aspect, the reducing agent is selected from the group consisting of TCEP and DTT. Preferably, the reducing agent is present at a final concentration between 0 and 100 mM, more preferably between 1 mM and 10 mM. Most preferably, the reducing agent is present at a final concentration of 5 mM.

In a preferred aspect of this first embodiment, the refolding method described above is carried out by dialysis or by gel filtration to yield a purified NS2/3 protease. In an important aspect, the soluble inactive NS2/3 protease is refolded using gel filtration. The elution buffer used contains LDAO, arginine-HCl and the reducing agent and the soluble inactive NS2/3 is maintained in the elution buffer for sufficient time to refold the NS2/3 protease. Collection of the main fractions allows recovery of a highly purified enzyme.

II. Method of activation

In accordance with a second embodiment of this invention, there is provided a method for producing an active NS2/3 protease comprising:

c) adding the soluble inactive NS2/3 protease obtained in step b), to a medium containing an activation agent so as to induce auto-cleavage of the NS2/3 protease.

In a preferred aspect of the second embodiment, the activation agent is selected from the group consisting of: glycerol, or a detergent such as CHAPS, Triton X-100, NP-40 and n-dodecyl-β-D-maltoside.

As an alternative to a this second embodiment of the invention, there is provided a method for producing an active NS2/3 protease comprising:

c) diluting the refolded inactive NS2/3 protease obtained in step b), in a medium containing an activation detergent to induce auto-cleavage of said NS2/3 protease.

Preferably, the LDAO remaining in the NS2/3 protease after dilution is at a final concentration below 0.25%. More preferably, the LDAO is diluted at a final concentration equal to or below 0.1%. Most preferably, the LDAO is diluted at a final concentration below 0.05%.

Preferably, the activation detergent may be selected from: CHAPS, Triton X-100, NP-40 and n-dodecyl-β-D-maltoside. More preferably, the activation detergent is CHAPS or n-dodecyl-β-D-maltoside.

Preferably, the activation detergent is at a final concentration of about 0.1% to about 3%. More preferably, the activation detergent is at a final concentration of about 0.1% to about 1%. Most preferably, the activation detergent is at a final concentration of 0.5%.

Further to the activation detergent, glycerol can also be added to aid in the activation of the refolded, inactive NS2/3 protease. Preferably, glycerol can be present at a final concentration between 0% and 60%. More preferably, glycerol can be present at a final concentration between 10% and 50%. Most preferably, glycerol is present at a final concentration of 30%.

Importantly, in a preferred aspect, the reducing agent is still present in the buffer or the activation/cleavage medium used for activation, albeit at a lower concentration than necessary for the refolding step. The reducing agent may be selected from the group consisting of TCEP and DTT. More preferably, the reducing agent is TCEP.

Preferably, the reducing agent is at a final concentration of between 1 mM and 100 mM. More preferably, the reducing agent is at a final concentration of between 1 mM and 10 mM. Preferably, the reducing agent is at a final concentration of 1 mM.

III. Method of measuring NS2/3 protease activity

In accordance with a preferred aspect of the third embodiment of the invention, there is provided a method of measuring the auto-cleavage activity of purified NS2/3 protease comprising:

c) incubating the refolded inactive NS2/3 protease obtained in step b) in a buffer containing an activation detergent, for sufficient time so that the NS2/3 protease autocleaves; and d) measuring the presence or absence of remaining uncleaved NS2/3 protease, cleavage products, or fragments thereof, as an indication of autocleavage.

Preferably, the refolded inactive NS2/3 protease is refolded and purified using gel filtration prior to carrying the above-mentioned assay.

Preferably, the activation detergent is: CHAPS, n-dodecyl-β-D-maltoside, NP-40 and Triton X-100. More preferably, the activation detergent is n-dodecyl-β-D-maltoside (DM) at a concentration of between 0.1% to 3%. More preferably, the activating detergent is n-dodecyl-β-D-maltoside at a concentration of about 0.1% to about 1%. Even most preferably, DM is at a final concentration of 0.5%.

A further activation agent such as glycerol can also be added to aid in the activation of the refolded, inactive NS2/3 protease. Preferably, glycerol can be present at a final concentration between 0% and 60%. More preferably, glycerol can be present at a final concentration between 10% and 50%. Most preferably, glycerol is at a final concentration of 30%.

Preferably, the NS2/3 protease is incubated in the cleavage buffer for at least 1 hour from 15° C. to 30° C. More preferably, the NS2/3 protease is incubated in the cleavage buffer for at least 1 hour from 15° C. to 25° C. Most preferably, the NS2/3 protease is incubated in the cleavage buffer for at least 1 hour at room temperature (about 23° C.).

In another aspect of the second embodiment, the cleavage reaction is stopped by denaturing the NS2/3 protease. More preferably, NS2/3 protease is denatured by heat. Most preferably, NS2/3 protease is denatured with SDS, to stop the autocleavage.

The cleavage products are preferably NS2 protein or NS3 protease. The amount of the NS2 protein or NS3 protease, or fragments thereof, may be measured using any one of the many techniques known to one of ordinary skill in the art. Examples of such techniques are enzymatic activity, immunoblot staining, chemiluminescence, fluorescence, or Coomassie staining. As an alternative, the amount of remaining uncleaved NS2/3 protease can also be measured as an indicator of cleavage.

IV. Methods of screening inhibitors

In a fourth embodiment, the invention provides an assay for screening potential inhibitors of the auto-cleavage activity of an active NS2/3 protease comprising:

c) incubating a sample of the refolded inactive NS2/3 protease obtained in step b) in a buffer containing an activation detergent, for sufficient time in the presence of, or absence of the potential inhibitor;

d) measuring the amount of cleavage products or fragments thereof, and e) comparing the amount of the cleavage products or fragments thereof, in the presence of, or absence of the potential inhibitor.

The sample of the active NS2/3 protease is preferably incubated for about 1 hour in the suitable medium with the candidate drug or ligand.

In a preferred aspect, the cleavage products are either NS2 protein or NS3 protease. Preferably, the presence or absence of either the NS2 protein or the NS3 protease, or fragments thereof, is analysed using enzymatic activity, immunoblot analysis, which comprises using an anti-NS3 protease antibody or a anti-histidine-tag antibody. As an alternative, the amount of remaining uncleaved NS2/3 protease can also be measured as an indicator of cleavage.

V. NS2/3 Protease, Polypeptides and Truncations/Nucleic Acid Molecules

Preferably, the NS2/3 protease is the full-length NS2/3 protease 810-1206 or a truncation thereof. More preferably, the NS2/3 protease is N-terminally truncated having its first amino acid corresponding to amino acid 815 to amino acid 906. Still more preferably, the N-terminal truncated protein having its first amino acid corresponding to amino acid 866 to 906. Even more preferably, the N-terminal truncated protein having its first amino acid corresponding to amino acid 890 to 904. Most preferably, there is provided a NS2/3 truncated protein having the minimal amino acid sequence from residues 904 to 1206 of the full-length NS2/3 protease. Even most preferably, the truncated NS2/3 protein consist of amino acids 904-1206 as numbered according to SEQ ID NO: 10.

In a fifth embodiment of the invention, there is provided an active NS2/3 polypeptide consisting of a truncated NS2/3 protease selected from the group consisting of: a sequence as defined according to SEQ ID NO: 2, 4, 10, 11, 12, 13, 14 and 15. Preferably, the NS2/3 protease has a sequence selected from the group consisting of: a sequence as defined according to SEQ ID NOS: 4, 10, 11, 12 and 15. More preferably, the NS2/3 protease has a sequence shown in SEQ ID NO: 4 or 10 or a functionally equivalent variant thereof. Most preferably, the NS2/3 protease has a sequence shown in SEQ ID NO: 4 or 10.

According to another aspect of the fifth embodiment of this invention, there is provided a refolded, inactive NS2/3 protease selected from the group consisting of: full length NS2/3 protease, a sequence as defined according to SEQ ID. NO: 2, 4, 10, 11, 12, 13, 14 and 15. More preferably, there is provided a refolded, inactive NS2/3 protease as defined according to SEQ ID. NO: 4 or 10.

According to a further aspect of the fifth embodiment, there is provided a polypeptide consisting of an amino acid sequence that has 90% identity over its length compared to the polypeptide as defined according to SEQ ID. NO: 2, 4, 10, 11, 12, 13, 14 and 15. More preferably, there is provided a polypeptide consisting of an amino acid sequence that has 90% identity over its length compared to the polypeptide as defined according to SEQ ID. NO: 4 or 10.

In another aspect of the fifth embodiment, there is provided a nucleic acid molecule encoding the amino acid sequence shown in SEQ ID NOS: 2, 4, 10, 11, 12, 13, 14 and 15 respectively.

Nucleic acid fragments that encode functionally equivalent variants of NS2/3 protease can be prepared by isolating a portion of residues from SEQ ID NO: 1, expressing the encoded portion 890-1206 of NS2/3 protease, e.g. by recombinant expression in a host cell, as described above, and assessing the ability of the portion to autocleave following purification and refolding.

Nucleic acid molecules of the present invention can be isolated using standard molecular biology techniques and the sequence information provided herein.

A nucleic acid molecule encompassing all or a portion of residues coding for amino acid 890-1206 can be isolated by the polymerase chain reaction (PCR) using appropriate oligonucleotide primers. For example, mRNA can be isolated from cells (e.g., by the guanidinium-thiocyanate extraction procedure of Chirgwin et al. (1979) *Biochemistry* 18: 5294–5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in SEQ ID NO: 1. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a NS2/3 protease nucleotide sequence can be prepared by standard synthetic techniques, e.g., using an automated DNA synthesizer.

In addition to naturally-occurring variants of the NS2/3 protease sequence that may exist in a viral population, one of ordinary skill in the art will further appreciate that changes may be introduced by mutation into the nucleotide sequence coding for amino acid 890 up to 1206, thereby leading to changes in the amino acid sequence of the encoded protein, that may or may not alter the functional activity of the NS2/3 protease. For example, nucleotide substitutions leading to amino acid substitutions at "non-essential" amino acid residues may be made in the sequence of SEQ ID NO: 1. A "non-essential" amino acid residue is a residue that can be altered from the full length sequence of NS2/3 protease (e.g., the sequence of SEQ ID NO: 2) without altering the functional activity of NS2/3 protease, whereas an "essential" amino acid residue is required for functional activity.

Accordingly, in another aspect, the invention pertains to nucleic acid molecules that encode NS2/3 protease that contain changes in amino acid residues that are essential for NS2/3 protease activity. Such NS2/3 protease mutants differ in amino acid sequence from SEQ ID NO: 10 and have lost their protease activity. Examples of such mutant NS2/3 proteases that may be used in the present invention are NS2/3 protease [904-1206]H952A (SEQ ID NO: 16), in which His-952 is replaced by Ala, NS2/3 protease[904-1206]ΔL1026A1027 (SEQ ID NO: 17), which corresponds to a deletion at the cleavage site residues between the NS2 and NS3 proteins and NS2/3 protease[904-1206]C993A in which the Cys993 is replaced by Ala (SEQ ID NO: 18).

EXAMPLES

The present invention is illustrated in further detail by the following non-limiting examples.

MATERIALS AND METHODS

Abbreviations:

| | |
|---|---|
| Ala: | alanine |
| ° C. | celsius |
| CHAPS: | 3-[(3-cholamidopropyl)dimethyl-ammonio]-1-propane sulfonate |
| CMC: | critical micellar concentration |
| DHFR: | dihydrofolate reductase |
| DNase: | deoxyribonuclease |
| DTPA: | N,N-bis[2-(bis[carboxymethyl]amino)ethyl]-glycine |
| DTT: | dithiothreitol |
| EDTA: | ethylenediaminetetraacetic acid |
| g: | gram |
| g: | relative centrifugal force |
| h: | hour |
| HCV: | hepatitis C virus |
| Hepes: | 4-(2-hydroxyethyl)-1-piperazine-ethanesulfonic acid |
| His: | histidine |
| His$_6$: | hexahistidine tag |
| HMK | heart muscle kinase |
| IPTG: | isopropyl-β-D-thiogalactopyranoside |
| kDa: | kilodalton |
| LDAO: | lauryldiethylamine oxide |
| Leu: | leucine |
| M: | molar |
| MBP: | maltose-binding protein |
| min: | minute |
| mL: | millilitre |
| mM: | millimolar |
| Octyl-POE: | n-octylpentaoxyethylene |
| PCR: | polymerase chain reaction |
| SDS-PAGE: | sodium dodecyl sulfate polyacrylamide gel electrophoresis |
| st: | streptavidin tag as described in Schmidt & Skerra, Prot. Engineering(1993) 6; 109–122 |

-continued

MATERIALS AND METHODS

Abbreviations:

| TCEP: | tris(2-carboxyethyl)phosphine hydrochloride |
|---|---|
| Tris: | tris[hydroxymethyl]aminomethane |
| μg: | microgram |
| μm: | micron |
| WT: | wild-type |
| w/v: | weight per volume |

Materials

The detergents CHAPS and Triton X-100 were obtained from Sigma, LDAO from Calbiochem, n-dodecyl-β-D-maltoside from Anatrace Inc., NP-40 from Roche and octyl-POE from Bachem. The reducing agents DTT and TCEP were obtained from Pharmacia Biotech and Pierce respectively. Arginine hydrochloride, glycerol, Hepes, imidazole and magnesium chloride were all obtained from Sigma. Guanidine hydrochloride and Tris were obtained from Gibco BRL, while IPTG and urea were from Roche. Sodium chloride and zinc chloride were obtained from Fisher and Aldrich respectively, EDTA was obtained from Ambion and DNase from Pharmacia Biotech. Restriction enzymes were obtained from Pharmacia Biotech. *E. coli* XL-1 Blue cells were obtained from Stratagene and BL21(DE3)pLysS cells from Novagen. FLAG™ is obtained from Eastman Kodak Company and corresponds to a peptide sequence that is recognized by an anti-FLAG antibody. $HMK_{tag}$ is a five-residue peptide (RRASV) that is a recognition sequence for the specific protein kinase HMK (Heart Muscle Kinase), therefore introducing a phosphorylation site (Blanar, M. and Rutter, W. (1992) Science 256:1014–1018).

Example 1
NS2/3 Full Length Construct:

The full length (810-1206) NS2/3 sequence was amplified by PCR from the HCV 1b-40 sequence (WO 99/07733 by Boehringer-Ingelheim (Canada), Ltd.) using two oligonucleotide primers, 5'-CCATGGACCGGGAGATGGCT-3' (SEQ ID NO: 5) for the N-terminus and 5'GGATCCTTAACCAC-CGAACTGCGGGTGACGCCAAGCGCTAC-TAGTCCGCAT GGTAGTTTCCAT-3' (SEQ ID NO: 6) for the C-terminus. This procedure introduces a NcoI site at the 5' end and a streptavidin tag "st" (Schmidt & Skerra, Prot. Engineering(1993) 6; 109–122) followed by a BamH1 site at the 3' end giving a nucleic acid molecule of SEQ ID NO: 1 (FIG. 1). The PCR product was inserted into the vector pCR™ 3 using the TA cloning® kit from Invitrogen. The insert was then transferred to a bacterial expression vector pET-11 d (Novagen) by cutting with EcoRI followed by Klenow treatment to create blunt ends followed by a partial digestion with NcoI. This construct was designated pET-11d-NS2/3 st. The DNA was transformed into XL-1 Blue *E. coli* cells, isolated and sequenced. The DNA was then transferred into *E. coli* BL21 (DE3) pLysS for protein production.

Example 2
NS2/3 N-terminal Deletion Mutants

The N-terminal deletion mutants 815*-1206, 827-1206, 855-1206, 866-1206, 904-1206 and 915-1206 were derived from the pET-11d/NS2/3 template that was designed with a NcoI site at the 5' end and within the NS3 domain at amino acid 1083. Following the template digestion with NcoI, the 3' end fragment and the vector were gel purified. The mutants were obtained by PCR using the appropriate synthetic oligonucleotides primers containing the NS2/3 sequence from nucleotides that encode the desired N-terminal residue up to amino acid 1083. The primers also introduced a NcoI site at the 5' end, such that the resulting inserts could be ligated to the gel purified fragment. The DNA was then transformed into *E. coli* XL-Blue cells, isolated and sequenced. Finally, the DNA was transferred into *E. coli* BL21(DE3)pLysS for protein production. Expression was verified by SDS-PAGE (FIGS. 2A, 2B, 2C).

* The numbering of this fragment is erroneous since the first methionine is part of the original sequence and should therefore be numbered "814". Therefore all reference to the truncation starting with 815 should be read as "814" as is correctly represented in SEQ ID NO: 11.

Example 3
NS2/3 N-terminal Truncation Mutant 4K-6H (904-1206)st-4K (SEQ ID NO: 4):

In this construct, four lysines were added at the N- and C-termini as well as a hexahistidine tag at the N-terminus. This construct was obtained using PCR and the pET-11d/NS2/3 st template with two primers containing the sequence for the tags as well as the NS2/3 sequence from nucleotides that encode amino acid residues 904-1206. The primers also introduced a NdeI and BamHI site at 5' and 3' end respectively. The insert was cloned into pET-11d and designated pET-11d 4K-6H—NS2/3 (904-1206)-st-4K (SEQ ID NO: 3). The DNA was transformed into *E. coli* XL-1 Blue cells, isolated and sequenced. The DNA was then transferred into *E. coli* BL21(DE3) pLysS for protein production.

For the truncated construct 904-1206, 4 primers and 2 successive PCR reactions were used. The primers used in the first PCR reaction were GCTCGAGCATCACCATCAC-CATCACACTAGTGCAGGCATAACCAAA (SEQ ID NO: 7) for the N-terminus and AACAATGGATCCT-TACTTTTTCTTTTTACCACCGAACTGCGGGTG (SEQ ID NO: 8) for the C-terminus. For the second PCR reaction, the primers used were ACCTGCCATATGAAAAA-GAAAAAGCTCGAGCATCACCATCACCAT (SEQ ID NO: 9) for the N-terminus and AACAATGGATCCT-TACTTTTTCTTTTTACCACCGAACTGCGGGTG (SEQ ID NO: 7) for the C-terminus.

Example 4
Enzyme Expression and Production

The HCV NS2/3 protease genotype 1b [904-1206] (FIG. 3) having a N-terminal hexahistidine tag was cloned in the pET-11d expression vector. Four lysine residues were also added at both N- and C-terminal ends to enhance the protein solubility, along with a streptavidin tag at the C-terminal end giving the nucleic acid molecule of SEQ ID NO: 3. The protease was expressed in *E. coli* BL21(DE3)pLysS following induction with 1 mM IPTG for 3 h at 37° C. A typical 4 L fermentation yielded approximately 20 g of wet cell paste. The cell paste can be stored at −80° C.

Example 5
Inclusion Bodies Extraction

Following thawing at 23° C., the cells were homogenized in lysis buffer (5 mL/g) consisting of 100 mM Tris, pH 8.0, 0.1% Triton X-100, 5 mM EDTA, 20 mM $MgCl_2$, 5 mM DTT followed by a DNase treatment (20 μg/mL) for 15 min at 4° C. and a centrifugation at 22,000×g for 1 h at 4° C. The cell pellet was then washed twice by homogenization (5 mL/g) in 100 mM Tris, pH 8.0, 2% Triton X-100, 5 mM EDTA, 2 M urea, 5 mM DTT and centrifuged at 22,000×g for 30 min at 4° C. Finally, cells were washed in 100 mM Tris, pH 8.0, 5 mM EDTA, 5 mM DTT. The inclusion bodies were recovered in the pellet by centrifugation at 22,000×g for 30 min at 4° C.

Example 6
a) Inclusion Bodies Extraction

To solubilize the inclusion bodies, the cell pellet was suspended in the extraction buffer (4 mL/g) consisting of 100 mM Tris, pH 8.0, 6 M guanidine-HCl, 0.5 M NaCl and kept in that buffer for 1 h at 23° C. The suspension was then centrifuged at 125,000×g for 30 min at 4° C. The resulting supernatant was filtered through a 0.22-$\mu$m filter. The clarified inclusion bodies extract can be stored at −80° C. until required.

b) 4K-6H—NS2/3 (904-1206)st-4K isolation from inclusion bodies

To isolate the 4K-6H—NS2/3 (904-1206)st-4K (SEQ ID NO. 4), the inclusion bodies extract was diluted 2-fold (to approx. 1 mg/mL) in 100 mM Tris, pH 8.0, 6 M guanidine-HCl, 0.5 M NaCl and applied on a Pharmacia Hi-Trap $Ni^{2+}$-chelating column. The isolated protein was typically eluted with 250 mM imidazole from a 50 to 500 mM imidazole linear gradient. The fractions corresponding to the major peak were pooled.

Example 7
Refolding and purification on Gel Filtration Column

To the preparation of isolated inclusion bodies was added 5 mM TCEP and 5 mM $ZnCl_2$. Following a 15 min incubation at 23° C., the sample was loaded on a Pharmacia Superose 12 gel filtration column. The 4K-6H—NS2/3 (904-1206)st-4K was then eluted in Tris 50 mM, pH 8.0, 0.5 M arginine-HCl, 1% LDAO, 5 mM TCEP yielding refolded NS2/3 protease. Only those fractions that correspond to the major peak (FIG. 4) are collected and pooled. Autocleavage was undetectable under these conditions. The purified, refolded inactive enzyme was stored at −80° C. in the elution buffer. Typically about 7 mg of refolded NS2/3 protease was obtained per liter of E. coli culture.

To overcome the problem of NS2/3 protease autocleavage, the refolding conditions were initially determined using either the His952Ala mutant (SEQ ID NO: 16) or the ΔLeu1026-Ala1027 mutant (SEQ ID NO: 17) of the 4K-6H—NS2/3 (904-1206)st-4K. Both these mutants are devoid of autocatalytic activity. The refolding was assessed indirectly based on the activity of the NS3 protease (FIG. 4) by incubating serial dilutions of the refolded enzyme with 5 $\mu$M of the internally quenched fluorogenic substrate anthranilyl-DDIVPAbu[C(O)—O] AMY(3-$NO_2$)TW—OH (SEQ ID NO: 19) in 50 mM Tris-HCl, pH 7.5, 30% glycerol, 1 mg/mL BSA and 1 mM TCEP for 30 or 60 min at 23° C. (specifically described in WO 99/07733 incorporated herein by reference). The proteolytic activity was monitored by the fluorescence change associated with cleavage of the substrate and the appearance of the fluorescent product anthranilyl-DDIVPAbu-COOH (SEQ ID NO: 20) on a BMG Galaxy 96-well plate reader (excitation filter: 355 nm; emission filter: 485 nm).

Then 4K-6H—NS2/3 (904-1206)st-4K was produced, purified and refolded according to the same protocol, resulting in a >95% pure enzyme. Proper refolding was confirmed by NS3 protease activity (FIG. 4, dotted line).

Example 8
Validation of Activity after Refolding
Cis-Cleavage Assay

The autocleavage reaction of the 4K-6H—NS2/3 (904-1206)st-4K was initiated by adding to the enzyme the cleavage buffer consisting of 50 mM Hepes, pH 7.0, 50% (w/v) glycerol, 0.1% CHAPS (FIG. 6) or 1% n-dodecyl-β-D-maltoside (FIGS. 7, 8) (NP-40 and Triton X-100 can also be used) and 1 mM TCEP. The assay mixture was then incubated for 3 h at 23° C. The reaction was stopped by heat denaturation of the enzyme in the presence of SDS. Cleavage at the NS2/3 junction was monitored by SDS-PAGE (15%) and immunoblot analyses using either a NS3 protease polyclonal antibody produced in-house or a commercially available hexahistidine-tag polyclonal antibody (Santa Cruz Biotechnology, Inc.) (FIG. 5).

Example 9
Heterogeneous Time-Resolved Fluorescence Assay

The NS2/3 protease is first immobilized on a nickel-chelating plate (FIG. 10). A europium-labeled anti-NS2 or anti-$FLAG_{tag}$ antibody is then added. One skilled in the art will recognize that many tags are available for labeling proteins. In this example, FLAG™ and HMK are used. Following binding of the antibody, a washing step is performed to remove the excess of antibody. Then, the autocleavage reaction is initiated by addition of the cleavage buffer. After the appropriate incubation time, the assay mixture is transferred in a second plate and the cleavage monitored by the measurement of the time-resolved fluorescence associated with the europium-labeled product. Cleavage of the NS2/3 protease may also be monitored by the decrease of the time-resolved europium fluorescence signal resulting from the unprocessed enzyme bound to the nickel-chelating plate.

As an alternative, a Strep-tag® containing —NS2/3 protease is incubated in the activating buffer and the autocleavage reaction is allowed to proceed (FIG. 14). The resulting Strep-tag NS3 fragment and the uncleaved Strep-tag NS2/3 protease is then immobilized on a streptavidin-coated plate. An europium-labeled anti-NS2 antibody is then added and time-resolved fluorescence associated with the bound europium-labeled antibody is measured.

Assay Protocol:
1—Autocleavage Reaction

In a 96-well polypropylene plate, are added sequentially: i) 20 $\mu$L of the assay buffer (50 mM Hepes, pH 7.5, 30% glycerol, 1 mM TCEP) with or without the presence of a test compound (potential inhibitor) and, ii) 10 $\mu$L of NS2/3 protease (at a final concentration of 200 nM) as purified according to Example 7. The autocleavage reaction is initiated by addition of 20 $\mu$L of the activation buffer (50 mM Hepes, pH 7.5, 30% glycerol, 0.5% n-dodecyl-β-D-maltoside, 1 mM TCEP) and is allowed to proceed for 1.5 hour at 30° C.

2—Binding to Streptavidin plate

In a 96-well white streptavidin-coated plate (Pierce), the autocleavage reaction mixture is diluted 5-fold in the assay buffer (50 mM Hepes, pH 7.5, 30% glycerol, 1 mM TCEP). Following a 1 h incubation at 23° C., the plate is washed with PBS, 0.05% Tween-20, 2 M guanidine-HCl.

3—Binding of $Eu^{+3}$-labeled anti-NS2

To the 96-well white streptavidin-coated plate[1], is then added the $Eu^{+3}$-labeled anti-NS2 at a final concentration of 35 nM in PBS, 0.05% Tween-20, 0.3% BSA, 1 $\mu$M biotin, 100 $\mu$M DTPA. Following a 1 h incubation at 23° C., the plate is washed with the DELFIA wash buffer (Perkin Elmer Wallac). Finally, the Enhancement solution (Perkin Elmer Wallac) is added and the time-resolved fluorescence measured on a Wallac 1420 VICTOR$^2$ multi-label counter.

[1]NOTE: Neutravidin plates can also be used.

Example 10
Homogeneous Time-Resolved Fluorescence Assay

The NS2/3 protease is labeled with a fluorescent europium chelate at one end and with a quencher of the europium fluorescence at the other end (FIG. 11). For example, an europium labeled anti-NS2 or anti-FLAG$_{tag}$ antibody is used as the fluorescent moiety, while the quencher of the europium fluorescence is either covalently bound to the enzyme or bound to a potent NS3 protease inhibitor. The enzymatic reaction is initiated by addition of the cleavage buffer. Upon autocleavage, the europium chelate and the quencher are separated resulting in an increase in the time-resolved europium fluorescence signal over time.

Example 11
Fluorescence Polarization Assay

A fluorescent probe, such as a potent NS3 protease inhibitor labeled with a fluorescent moiety, is added to a NS2/3 protease containing solution (FIG. 12). The autocleavage reaction is initiated by addition of the cleavage buffer. The change in fluorescence polarization of the probe upon autocleavage is monitored over time. Alternatively, an immobilized NS2/3 protease on a nickel-chelating plate may also be used. Following incubation of the enzyme with the fluorescent probe, the autocleavage reaction is initiated by addition of the cleavage buffer. After the appropriate incubation time, the cleavage is monitored by measuring the change in fluorescence polarization of the probe.

Example 12
Radiometric Assay

The NS2/3 protease is first immobilized on a nickel-chelating plate (FIG. 13). The HMK$_{tag}$ is then phosphorylated using the protein kinase A and a radiolabeled substrate. After completion of the phosphorylation reaction, the plate is washed and the autocleavage reaction initiated by adding the cleavage buffer. After the appropriate incubation time, the reaction is quantitated either by measuring the amount of radiolabeled product released in the assay solution or the amount of radiolabeled unprocessed NS2/3 protease. Alternatively, the phosphorylation reaction may be performed first followed by immobilization on the nickel-chelating plate.

Example 13
NS2/3 Protease Inhibition

NS2/3 protease cleavage-site derived peptides were evaluated as potentially competing substrates (Table I). NS2/3 protease cleavage-site derived peptides and NS4A-derived peptides were synthesized in-house using the standard solid-phase methodology or were made by Multiple Peptide Systems (San Diego, Calif.). Various concentrations of peptides were pre-incubated with 0.54 μM NS2/3 protease for 30 min at 23° C. in 50 mM Hepes, pH 7.0, and 50% (w/v) glycerol. The autocleavage reaction was initiated by addition of n-dodecyl-β-D-maltoside to a final concentration of 0.5%. The final DMSO content never exceeded 5% (v/v). The resulting mixture was then incubated for 3 h at 23° C. The reaction was stopped and quantified.

None of the NS2/3 protease cleavage-site derived peptides were cleaved in trans (data not shown). The peptide spanning residues P10–P10' of the NS2/3 junction (peptide 1) inhibited the autocleavage with an IC$_{50}$ of 270 μM, whereas the peptide substrate spanning residues P6–P6' (peptide 4) was less potent with an IC$_{50}$ of 630 μM. Among the corresponding cleavage-site products, the most active was the peptide SFEGQGWRLL (IC$_{50}$=90 μM, SEQ ID NO: 21), the N-terminal product of peptide 1.

TABLE I

Inhibition of NS2/3 Autocleavage by Peptides[a]

| Peptide # | Sequence | | IC$_{50}$ (μM[b]) |
|---|---|---|---|
| NS2/3 protease cleavage site-derived peptides[c] | | | |
| 1 | SFEGQGWRLL-APITAYSQQT | | 270 |
| 2 | SFEGQGWRLL | (SEQ ID NO:21) | 90 |
| 3 | APITAYSQQT | (SEQ ID NO:23) | >1000 |
| 4 | KGWRLL-APITAY | (SEQ ID NO:24) | 630 |
| 5 | APITAY | (SEQ ID NO:25) | 1000 |

[a]Peptides were prepared as 20 mM stock solution in DMSO. The final DMSO content never exceeded 5% (v/v).
[b]Assay was performed in the presence of 0.54 μM NS2/3 protease.
[c]The hyphen indicates the cleavage site between P1 and P1' residues.

Discussion

To date, production of native NS2 alone or linked to NS3 has been hampered by its hydrophobic nature, only low level expression being achieved. A N-terminal truncation study has allowed for the identification of the NS2/3 protease [904-1206] (FIG. 3). This truncation was expressed at high levels in *E. coli* upon IPTG induction (FIGS. 2B and 2C, lane 904) and was active as shown by the presence of the NS3 protease cleavage product (FIGS. 2A and 2C, lane 904). However, NS2/3 protease [904-1206] was recovered only in the insoluble fraction as inclusion bodies. Use of soluble fusion partners, such as maltose-binding protein and thioredoxin, was unsuccessful in increasing the solubility of the protease upon expression (data not shown).

Maintenance of low concentration of chaotropic agent or polar additive such as 0.5 M arginine-HCl was important to maintain the 4K-6H—NS2/3 (904-1206)st-4K (FIG. 9B, SEQ ID NO: 4) in solution during the refolding process. Arginine-HCl is a polar additive that slightly destabilizes proteins in a manner comparable to low concentration of chaotrophs. It is hypothesized that arginine-HCl may increase the solubilization of folding intermediates (Lin, T.-Y. et al. (1996) *Protein Sci.* 5:372–381.).

A detergent was also required for refolding to reduce and/or suppress aggregation upon substituting the denaturing buffer by the refolding buffer. The detergents LDAO, n-dodecyl-β-D-maltoside and octyl-POE were evaluated for their ability to promote refolding of 4K-6H—NS2/3 (904-1206)st-4K at concentrations at or higher than their respective CMC value of 0.03%, 0.01% and 0.25% (in water). No refolding was detectable in the presence of octyl-POE. LDAO and n-dodecyl-β-D-maltoside were found to efficiently refold the enzyme. However, in addition to its refolding capability, n-dodecyl-β-D-maltoside was found to induce activation of 4K-6H—NS2/3 (904-1206)st-4K. LDAO was selected since, unexpectedly, it allowed refolding and reconstitution of the NS3 protease activity without promoting autocleavage. Finally, the inventors have found that the presence of a reducing agent, either DTT or TCEP, was necessary for refolding the enzyme.

Several cleavage/activation detergents were evaluated for their ability to promote autocleavage of the 4K-6H—NS2/3 (904-1 206)st-4K. Autoprocessing was observed upon addition of CHAPS in the assay buffer from Example 7 (FIG. 6, lanes 2–5). Similar autoprocessing was also observed with n-dodecyl-β-D-maltoside, NP-40 and Triton X-100, although 0.5% and 1% n-dodecyl-β-D-maltoside appeared to be superior. Poor processing was, however, observed in the presence of octyl-POE while almost none was observed with LDAO (data not shown). In addition to the cleavage/activation detergents, glycerol was also found to promote autocleavage (FIG. 6, lane 1). Interestingly, low levels of cleavage were observed with 0% glycerol, whereas substantially enhanced cleavage was observed when both glycerol and cleavage/activation detergent were added to the assay buffer (FIG. 6, lane 6).

LDAO, which was used during refolding, inhibited the autoprocessing, such that the autocleavage reaction could only be initiated by dilution of the enzyme in the appropriate cleavage/activation buffer and dilution of the LDAO to a concentration below about 0.25%.

The NS2/3 protease's activity was confirmed by SDS-PAGE and immunoblot analyses (FIG. 7) and by the absence of cleavage products for the corresponding His952Ala mutant (FIG. 8). Furthermore, no change in the activity was observed in the presence of potent NS3 protease inhibitors (data not shown). Finally, N-terminal sequencing of both cis-cleavage products confirmed that the cleavage occurred between the residues Leu1026 and Ala1027.

The cleavage site derived-peptide substrates P10–P10' and P6–P6' were evaluated as potentially competing substrates. In a well defined assay system using purified NS2/3 (904-1206) and an optimized cleavage buffer (containing 50% glycerol and 0.5% n-dodecyl-β-D-maltoside), the P10–P10' and P6–P6' peptides inhibited NS2/3 processing with $IC_{50}$'s of 270 and 630 μM respectively; yet under identical assay conditions, no trans-cleavage of the peptides was observed (data not shown). The results suggest non-productive binding of the peptide substrate at the active site. Notably, the shorter P10-P1 N-terminal cleavage product peptide was the best inhibitor with an $IC_{50}$ of 90 μM, whereas the corresponding C-terminal product was devoid of inhibitory activity.

What is claimed is:

1. A method of producing a refolded, inactive HCV NS2/3 protease, comprising the steps of:
   a) isolating said protease in the presence of a chaotropic agent;
   b) refolding said isolated protease by contacting it with a reducing agent, and lauryldiethylamine oxide (LDAO) in the presence of reduced concentration of said chaotropic agent or a polar additive.

2. The method according to claim 1, wherein said LDAO is at a final concentration at, or above critical micelle concentration.

3. The method according to claim 2, wherein said LDAO is at a final concentration between 0.003% and 1%.

4. The method according to claim 3, wherein said LDAO is at a final concentration between 0.03% and 1%.

5. The method according to claim 4, wherein said LDAO is at a final concentration of 1%.

6. The method according to claim 1, wherein in step a) said chaotropic agent is selected from the group consisting of: guanidine-HCl, guanidine or urea.

7. The method according to claim 6, wherein said chaotropic agent is at high concentration between 5M and 8M.

8. The method according to claim 7, wherein said chaotropic agent is guanidine or guanidine-HCl, each at a final concentration of 6M or urea at a final concentration of 8M.

9. The method according to claim 8, wherein said chaotropic agent is 6M guanidine-HCl.

10. The method according to claim 1, wherein in step b), the chaotropic agent or polar additive is selected from the group consisting of: guanidine, guanidine-HCl, urea and arginine-HCl.

11. The method according to claim 10, wherein guanidine-HCl or arginine-HCl is used.

12. The method according to claim 11, wherein arginine-HCl is used.

13. The method according to claim 12, wherein said arginine-HCl is at a final concentration between 0.25M and 2M.

14. The method according to claim 13, wherein said arginine-HCl is at a final concentration between 0.5M and 1 M.

15. The method according to claim 14, wherein said arginine-HCl is at a final concentration of 0.5M.

16. The method according to claim 1, wherein the reducing agent is selected from the group consisting of TCEP and DTT.

17. The method according to claim 16, wherein the reducing agent is TCEP at a final concentration of 5 mM.

18. The method according to claim 1, wherein said protease is isolated from cellular inclusion bodies.

19. The method according to claim 1, wherein said refolding is carried out by dialysis or by gel filtration to yield a purified NS2/3 protease.

20. The method according to claim 19, wherein said refolding is carried out by gel filtration.

21. The method according to claim 1, wherein said NS2/3 protease is the full length NS2/3 protease or a truncation thereof having as its N-terminal residue any one amino acid from amino acid 810 to amino acid 906.

22. The method according to claim 21, wherein said NS2/3 protease has the minimal amino acid sequence from residues 904 to 1206 of the HCV 1b-40 full-length NS2/3 protease.

23. The method according to claim 22, wherein said NS2/3 protease is consisting of a truncated NS2/3 protease as defined according to SEQ ID. NO: 10.

24. A method for producing an active NS2/3 protease further comprising:
   c) diluting said refolded inactive NS2/3 protease produced by the method of claim 1, in a medium containing an activation detergent to induce auto-cleavage of said NS2/3 protease.

25. The method according to claim 24, wherein said LDAO is diluted at a final concentration equal or below 0.1%.

26. The method according to claim 24, wherein In step c) glycerol is further added.

27. The method according to claim 26, wherein said glycerol is at a final concentration of between 10% and 50%.

28. The method according to claim 24, wherein the activation detergent is selected from the group consisting of: CHAPS, Triton X-100, NP-40 and n-dodecyl-β-D-maltoside.

29. The method according to claim 28, wherein the activation detergent is at a final concentration between 0.1% and 1%.

30. The method according to claim 29, wherein the activation detergent is CHAPS.

31. The method according to claim 29 wherein the activation detergent is n-dodecyl-β-D-maltoside.

32. A method for measuring the auto-cleavage activity of a NS2/3 protease further comprising:
   d) incubating the active NS2/3 protease produced by the method of claim 24 for sufficient time to induce auto-cleavage of the NS2/3 protease and produce cleavage products or fragments thereof; and
   e) measuring the presence or absence of uncleaved NS2/3 protease, cleavage products or fragments thereof.

33. The method according to claim 32, wherein step d) is carried out at a temperature between 15° C. and 30° C.

34. The method according to claim 33, wherein step d) is carried out at a temperature between 15° C. and 25° C.

35. The method according to claim 34, wherein step d) is carried out at room temperature.

36. An assay for screening a potential inhibitor of the auto-cleavage activity of an active NS2/3 protease comprising:
 a) carrying out the method according to claim 32 in the presence of, or absence of the potential inhibitor;
 b) comparing the amount of uncleaved NS2/3 protease, cleavage products or fragments thereof, in the presence of, or absence of the potential inhibitor.

37. A composition comprising an isolated HCV NS2/3 protease selected from full length NS2/3 protease, a truncation thereof or a sequence as defined according to SEQ ID NOs: 2, 4, 10, 11, 12, 13, 14 and 15, wherein said protease is in a solution comprising a sufficient concentration of LDAO to prevent auto-cleavage of said protease.

* * * * *

SEQUENCE LISTING

```
<160> NUMBER OF SEQ ID NOS: 25

<210> SEQ ID NO 1
<211> LENGTH: 1230
<212> TYPE: DNA
<213> ORGANISM: HCV
<220> FEATURE:
<221> NAME/KEY: CDS
<222> LOCATION: (1)...(1230)

<400> SEQUENCE: 1 atg gac cgg gag atg gct gca tcg tgc gga ggc gcg gtt ttc ata ggt      48
Met Asp Arg Glu Met Ala Ala Ser Cys Gly Gly Ala Val Phe Ile Gly
1               5                  10                  15 ctt gca ctc ttg acc ttg tca cca tac tat aaa gtg ctc ctc gct agg      96
Leu Ala Leu Leu Thr Leu Ser Pro Tyr Tyr Lys Val Leu Leu Ala Arg
                20                  25                  30 ctc ata tgg tgg tta cag tat tta atc acc aga gtc gag gcg cac ttg     144
Leu Ile Trp Trp Leu Gln Tyr Leu Ile Thr Arg Val Glu Ala His Leu
            35                  40                  45 caa gtg tgg atc ccc cct ctc aat gtt cgg gga ggc cgc gat gcc atc     192
Gln Val Trp Ile Pro Pro Leu Asn Val Arg Gly Gly Arg Asp Ala Ile
        50                  55                  60 atc ctc ctc acg tgc gca gtc cac cca gag cta atc ttt gac atc acc     240
Ile Leu Leu Thr Cys Ala Val His Pro Glu Leu Ile Phe Asp Ile Thr
65                  70                  75                  80 aaa ctc ctg ctc gcc ata ttc ggt ccg ctc atg gtg ctc cag gca ggc     288
Lys Leu Leu Leu Ala Ile Phe Gly Pro Leu Met Val Leu Gln Ala Gly
                85                  90                  95 ata acc aaa gtg ccg tac ttc gtg cgt gcg cag ggg ctc att cgt gcg     336
Ile Thr Lys Val Pro Tyr Phe Val Arg Ala Gln Gly Leu Ile Arg Ala
                100                 105                 110 tgt atg ttg gtg cgg aag gct gcg ggg ggt cat tat gtc caa atg gcc     384
Cys Met Leu Val Arg Lys Ala Ala Gly Gly His Tyr Val Gln Met Ala
```

```
                    115                 120                 125
ttc atg aag cta gct gcg ctg aca ggt acg tac gtt tat gac cat ctc     432
Phe Met Lys Leu Ala Ala Leu Thr Gly Thr Tyr Val Tyr Asp His Leu
    130                 135                 140 act cca ttg cag gat tgg gcc cac gcg ggc cta cga gac ctt gca gtg     480
Thr Pro Leu Gln Asp Trp Ala His Ala Gly Leu Arg Asp Leu Ala Val
145                 150                 155                 160 gcg gta gag ccc gtc atc ttc tct gac atg gag gtc aag atc atc acc     528
Ala Val Glu Pro Val Ile Phe Ser Asp Met Glu Val Lys Ile Ile Thr
                165                 170                 175 tgg ggg gcg gac acc gcg gca tgc ggg gac atc att tca ggt ctg ccc     576
Trp Gly Ala Asp Thr Ala Ala Cys Gly Asp Ile Ile Ser Gly Leu Pro
            180                 185                 190 gtc tcc gct cga agg gga agg gag ata ctc ctg gga ccg gcc gat aat     624
Val Ser Ala Arg Arg Gly Arg Glu Ile Leu Leu Gly Pro Ala Asp Asn
        195                 200                 205 ttt gaa ggg cag ggg tgg cga ctc ctt gcg ccc atc acg gcc tac tcc     672
Phe Glu Gly Gln Gly Trp Arg Leu Leu Ala Pro Ile Thr Ala Tyr Ser
    210                 215                 220 caa cag aca cgg ggc cta ctt ggt tgc atc atc acc agc ctc aca ggc     720
Gln Gln Thr Arg Gly Leu Leu Gly Cys Ile Ile Thr Ser Leu Thr Gly
225                 230                 235                 240 cgg gac aag aac cag gtc gag ggg gag gtt caa gtg gtc tcc acc gct     768
Arg Asp Lys Asn Gln Val Glu Gly Glu Val Gln Val Val Ser Thr Ala
                245                 250                 255 aca caa tct ttc ctg gcg acc tgc gtc aac ggc gtg tgt tgg act gtc     816
Thr Gln Ser Phe Leu Ala Thr Cys Val Asn Gly Val Cys Trp Thr Val
            260                 265                 270 ttc cat ggc gcc ggc tca aag acc ttg gcc ggc ccc aaa ggc cca atc     864
Phe His Gly Ala Gly Ser Lys Thr Leu Ala Gly Pro Lys Gly Pro Ile
        275                 280                 285 acc cag atg tac act aat gtg gac cag gac ctc gtc ggc tgg cag gcg     912
Thr Gln Met Tyr Thr Asn Val Asp Gln Asp Leu Val Gly Trp Gln Ala
    290                 295                 300 ccc cct ggg gcg cgc tcc atg aca cca tgc acc tgc ggc agc tcg gac     960
Pro Pro Gly Ala Arg Ser Met Thr Pro Cys Thr Cys Gly Ser Ser Asp
305                 310                 315                 320 ctc tat ttg gtc acg aga cat gcc gac gtc att ccg gtg cgc cgg cgg    1008
Leu Tyr Leu Val Thr Arg His Ala Asp Val Ile Pro Val Arg Arg Arg
                325                 330                 335 ggc gac agt agg ggg agc ctg ctc tcc ccc agg cct gtc tcc tac ttg    1056
Gly Asp Ser Arg Gly Ser Leu Leu Ser Pro Arg Pro Val Ser Tyr Leu
            340                 345                 350 aag ggc tct tcg ggt ggc cca ctg ctc tgc cct tcg ggg cac gct gtg    1104
Lys Gly Ser Ser Gly Gly Pro Leu Leu Cys Pro Ser Gly His Ala Val
        355                 360                 365 ggc atc ttc cgg gct gct gtg tgc acc cgg ggg gtt gca aaa gcg gtg    1152
Gly Ile Phe Arg Ala Ala Val Cys Thr Arg Gly Val Ala Lys Ala Val
    370                 375                 380 gac ttc ata cct gtt gag tct atg gaa act acc atg cgg act agt agc    1200
Asp Phe Ile Pro Val Glu Ser Met Glu Thr Thr Met Arg Thr Ser Ser
385                 390                 395                 400 gct tgg cgt cac ccg cag ttc ggt ggt taa                            1230
Ala Trp Arg His Pro Gln Phe Gly Gly *
                405

<210> SEQ ID NO 2
<211> LENGTH: 409
<212> TYPE: PRT
<213> ORGANISM: HCV
```

<400> SEQUENCE: 2

```
Met Asp Arg Glu Met Ala Ala Ser Cys Gly Gly Ala Val Phe Ile Gly
  1               5                  10                  15
Leu Ala Leu Leu Thr Leu Ser Pro Tyr Tyr Lys Val Leu Leu Ala Arg
             20                  25                  30
Leu Ile Trp Trp Leu Gln Tyr Leu Ile Thr Arg Val Glu Ala His Leu
         35                  40                  45
Gln Val Trp Ile Pro Pro Leu Asn Val Arg Gly Gly Arg Asp Ala Ile
     50                  55                  60
Ile Leu Leu Thr Cys Ala Val His Pro Glu Leu Ile Phe Asp Ile Thr
 65                  70                  75                  80
Lys Leu Leu Leu Ala Ile Phe Gly Pro Leu Met Val Leu Gln Ala Gly
                 85                  90                  95
Ile Thr Lys Val Pro Tyr Phe Val Arg Ala Gln Gly Leu Ile Arg Ala
             100                 105                 110
Cys Met Leu Val Arg Lys Ala Ala Gly Gly His Tyr Val Gln Met Ala
         115                 120                 125
Phe Met Lys Leu Ala Ala Leu Thr Gly Thr Tyr Val Tyr Asp His Leu
    130                 135                 140
Thr Pro Leu Gln Asp Trp Ala His Ala Gly Leu Arg Asp Leu Ala Val
145                 150                 155                 160
Ala Val Glu Pro Val Ile Phe Ser Asp Met Glu Val Lys Ile Ile Thr
                165                 170                 175
Trp Gly Ala Asp Thr Ala Ala Cys Gly Asp Ile Ile Ser Gly Leu Pro
            180                 185                 190
Val Ser Ala Arg Arg Gly Arg Glu Ile Leu Leu Gly Pro Ala Asp Asn
        195                 200                 205
Phe Glu Gly Gln Gly Trp Arg Leu Leu Ala Pro Ile Thr Ala Tyr Ser
    210                 215                 220
Gln Gln Thr Arg Gly Leu Leu Gly Cys Ile Ile Thr Ser Leu Thr Gly
225                 230                 235                 240
Arg Asp Lys Asn Gln Val Glu Gly Glu Val Gln Val Val Ser Thr Ala
                245                 250                 255
Thr Gln Ser Phe Leu Ala Thr Cys Val Asn Gly Val Cys Trp Thr Val
            260                 265                 270
Phe His Gly Ala Gly Ser Lys Thr Leu Ala Gly Pro Lys Gly Pro Ile
        275                 280                 285
Thr Gln Met Tyr Thr Asn Val Asp Gln Asp Leu Val Gly Trp Gln Ala
    290                 295                 300
Pro Pro Gly Ala Arg Ser Met Thr Pro Cys Thr Cys Gly Ser Ser Asp
305                 310                 315                 320
Leu Tyr Leu Val Thr Arg His Ala Asp Val Ile Pro Val Arg Arg Arg
                325                 330                 335
Gly Asp Ser Arg Gly Ser Leu Leu Ser Pro Arg Pro Val Ser Tyr Leu
            340                 345                 350
Lys Gly Ser Ser Gly Gly Pro Leu Leu Cys Pro Ser Gly His Ala Val
        355                 360                 365
Gly Ile Phe Arg Ala Ala Val Cys Thr Arg Gly Val Ala Lys Ala Val
    370                 375                 380
Asp Phe Ile Pro Val Glu Ser Met Glu Thr Thr Met Arg Thr Ser Ser
385                 390                 395                 400
Ala Trp Arg His Pro Gln Phe Gly Gly
```

-continued

405

<210> SEQ ID NO 3
<211> LENGTH: 1011
<212> TYPE: DNA
<213> ORGANISM: HCV
<220> FEATURE:
<221> NAME/KEY: CDS
<222> LOCATION: (1)...(1005)

<400> SEQUENCE: 3

| | | | | | | | | | | | | | | | | |
|---|---|---|---|---|---|---|---|---|---|---|---|---|---|---|---|---|
| atg | aaa | aag | aaa | aag | ctc | gag | cat | cac | cat | cac | cat | cac | act | agt | gca | 48 |
| Met | Lys | Lys | Lys | Lys | Leu | Glu | His | His | His | His | His | His | Thr | Ser | Ala | |
| 1 | | | | 5 | | | | | 10 | | | | | 15 | | |
| ggc | ata | acc | aaa | gtg | ccg | tac | ttc | gtg | cgt | gcg | cag | ggg | ctc | att | cgt | 96 |
| Gly | Ile | Thr | Lys | Val | Pro | Tyr | Phe | Val | Arg | Ala | Gln | Gly | Leu | Ile | Arg | |
| | | | 20 | | | | | 25 | | | | | 30 | | | |
| gcg | tgt | atg | ttg | gtg | cgg | aag | gct | gcg | ggg | ggt | cat | tat | gtc | caa | atg | 144 |
| Ala | Cys | Met | Leu | Val | Arg | Lys | Ala | Ala | Gly | Gly | His | Tyr | Val | Gln | Met | |
| | | 35 | | | | | 40 | | | | | 45 | | | | |
| gcc | ttc | atg | aag | cta | gct | gcg | ctg | aca | ggt | acg | tac | gtt | tat | gac | cat | 192 |
| Ala | Phe | Met | Lys | Leu | Ala | Ala | Leu | Thr | Gly | Thr | Tyr | Val | Tyr | Asp | His | |
| | 50 | | | | | 55 | | | | | 60 | | | | | |
| ctc | act | cca | ttg | cag | gat | tgg | gcc | cac | gcg | ggc | cta | cga | gac | ctt | gca | 240 |
| Leu | Thr | Pro | Leu | Gln | Asp | Trp | Ala | His | Ala | Gly | Leu | Arg | Asp | Leu | Ala | |
| 65 | | | | | 70 | | | | | 75 | | | | | 80 | |
| gtg | gcg | gta | gag | ccc | gtc | atc | ttc | tct | gac | atg | gag | gtc | aag | atc | atc | 288 |
| Val | Ala | Val | Glu | Pro | Val | Ile | Phe | Ser | Asp | Met | Glu | Val | Lys | Ile | Ile | |
| | | | | 85 | | | | | 90 | | | | | 95 | | |
| acc | tgg | ggg | gcg | gac | acc | gcg | gca | tgc | ggg | gac | atc | att | tca | ggt | ctg | 336 |
| Thr | Trp | Gly | Ala | Asp | Thr | Ala | Ala | Cys | Gly | Asp | Ile | Ile | Ser | Gly | Leu | |
| | | | | 100 | | | | | 105 | | | | | 110 | | |
| ccc | gtc | tcc | gct | cga | agg | gga | agg | gag | ata | ctc | ctg | gga | ccg | gcc | gat | 384 |
| Pro | Val | Ser | Ala | Arg | Arg | Gly | Arg | Glu | Ile | Leu | Leu | Gly | Pro | Ala | Asp | |
| | | | 115 | | | | | 120 | | | | | 125 | | | |
| aat | ttt | gaa | ggg | cag | ggg | tgg | cga | ctc | ctt | gcg | ccc | atc | acg | gcc | tac | 432 |
| Asn | Phe | Glu | Gly | Gln | Gly | Trp | Arg | Leu | Leu | Ala | Pro | Ile | Thr | Ala | Tyr | |
| | 130 | | | | | 135 | | | | | 140 | | | | | |
| tcc | caa | cag | aca | cgg | ggc | cta | ctt | ggt | tgc | atc | atc | acc | agc | ctc | aca | 480 |
| Ser | Gln | Gln | Thr | Arg | Gly | Leu | Leu | Gly | Cys | Ile | Ile | Thr | Ser | Leu | Thr | |
| 145 | | | | | 150 | | | | | 155 | | | | | 160 | |
| ggc | cgg | gac | aag | aac | cag | gtc | gag | ggg | gag | gtt | caa | gtg | gtc | tcc | acc | 528 |
| Gly | Arg | Asp | Lys | Asn | Gln | Val | Glu | Gly | Glu | Val | Gln | Val | Val | Ser | Thr | |
| | | | | 165 | | | | | 170 | | | | | 175 | | |
| gct | aca | caa | tct | ttc | ctg | gcg | acc | tgc | gtc | aac | ggc | gtg | tgt | tgg | act | 576 |
| Ala | Thr | Gln | Ser | Phe | Leu | Ala | Thr | Cys | Val | Asn | Gly | Val | Cys | Trp | Thr | |
| | | | 180 | | | | | 185 | | | | | 190 | | | |
| gtc | ttc | cat | ggc | gcc | ggc | tca | aag | acc | ttg | gcc | ggc | ccc | aaa | ggc | cca | 624 |
| Val | Phe | His | Gly | Ala | Gly | Ser | Lys | Thr | Leu | Ala | Gly | Pro | Lys | Gly | Pro | |
| | | 195 | | | | | 200 | | | | | 205 | | | | |
| atc | acc | cag | atg | tac | act | aat | gtg | gac | cag | gac | ctc | gtc | ggc | tgg | cag | 672 |
| Ile | Thr | Gln | Met | Tyr | Thr | Asn | Val | Asp | Gln | Asp | Leu | Val | Gly | Trp | Gln | |
| | 210 | | | | | 215 | | | | | 220 | | | | | |
| gcg | ccc | cct | ggg | gcg | cgc | tcc | atg | aca | cca | tgc | acc | tgc | ggc | agc | tcg | 720 |
| Ala | Pro | Pro | Gly | Ala | Arg | Ser | Met | Thr | Pro | Cys | Thr | Cys | Gly | Ser | Ser | |
| 225 | | | | | 230 | | | | | 235 | | | | | 240 | |
| gac | ctc | tat | ttg | gtc | acg | aga | cat | gcc | gac | gtc | att | ccg | gtg | cgc | cgg | 768 |
| Asp | Leu | Tyr | Leu | Val | Thr | Arg | His | Ala | Asp | Val | Ile | Pro | Val | Arg | Arg | |
| | | | | 245 | | | | | 250 | | | | | 255 | | |
| cgg | ggc | gac | agt | agg | ggg | agc | ctg | ctc | tcc | ccc | agg | cct | gtc | tcc | tac | 816 |
| Arg | Gly | Asp | Ser | Arg | Gly | Ser | Leu | Leu | Ser | Pro | Arg | Pro | Val | Ser | Tyr | |

-continued

```
ttg aag ggc tct tcg ggt ggc cca ctg ctc tgc cct tcg ggg cac gct      864
Leu Lys Gly Ser Ser Gly Gly Pro Leu Leu Cys Pro Ser Gly His Ala
        275                 280                 285 gtg ggc atc ttc cgg gct gct gtg tgc acc cgg ggg gtt gca aaa gcg      912
Val Gly Ile Phe Arg Ala Ala Val Cys Thr Arg Gly Val Ala Lys Ala
    290                 295                 300 gtg gac ttc ata cct gtt gag tct atg gaa act acc atg cgg act agt      960
Val Asp Phe Ile Pro Val Glu Ser Met Glu Thr Thr Met Arg Thr Ser
305                 310                 315                 320 agc gct tgg cgt cac ccg cag ttc ggt ggt aaa aag aaa aag taa         1005
Ser Ala Trp Arg His Pro Gln Phe Gly Gly Lys Lys Lys Lys *
                325                 330 ggatcc                                                              1011
```

<210> SEQ ID NO 4
<211> LENGTH: 334
<212> TYPE: PRT
<213> ORGANISM: HCV

<400> SEQUENCE: 4

```
Met Lys Lys Lys Lys Leu Glu His His His His His Thr Ser Ala
 1               5                  10                  15

Gly Ile Thr Lys Val Pro Tyr Phe Val Arg Ala Gln Gly Leu Ile Arg
            20                  25                  30

Ala Cys Met Leu Val Arg Lys Ala Ala Gly Gly His Tyr Val Gln Met
        35                  40                  45

Ala Phe Met Lys Leu Ala Ala Leu Thr Gly Thr Tyr Val Tyr Asp His
    50                  55                  60

Leu Thr Pro Leu Gln Asp Trp Ala His Ala Gly Leu Arg Asp Leu Ala
65                  70                  75                  80

Val Ala Val Glu Pro Val Ile Phe Ser Asp Met Glu Val Lys Ile Ile
                85                  90                  95

Thr Trp Gly Ala Asp Thr Ala Ala Cys Gly Asp Ile Ile Ser Gly Leu
            100                 105                 110

Pro Val Ser Ala Arg Arg Gly Arg Glu Ile Leu Leu Gly Pro Ala Asp
        115                 120                 125

Asn Phe Glu Gly Gln Gly Trp Arg Leu Leu Ala Pro Ile Thr Ala Tyr
    130                 135                 140

Ser Gln Gln Thr Arg Gly Leu Leu Gly Cys Ile Ile Thr Ser Leu Thr
145                 150                 155                 160

Gly Arg Asp Lys Asn Gln Val Glu Gly Glu Val Gln Val Val Ser Thr
                165                 170                 175

Ala Thr Gln Ser Phe Leu Ala Thr Cys Val Asn Gly Val Cys Trp Thr
            180                 185                 190

Val Phe His Gly Ala Gly Ser Lys Thr Leu Ala Gly Pro Lys Gly Pro
        195                 200                 205

Ile Thr Gln Met Tyr Thr Asn Val Asp Gln Asp Leu Val Gly Trp Gln
    210                 215                 220

Ala Pro Pro Gly Ala Arg Ser Met Thr Pro Cys Thr Cys Gly Ser Ser
225                 230                 235                 240

Asp Leu Tyr Leu Val Thr Arg His Ala Asp Val Ile Pro Val Arg Arg
                245                 250                 255

Arg Gly Asp Ser Arg Gly Ser Leu Leu Ser Pro Arg Pro Val Ser Tyr
            260                 265                 270
```

```
Leu Lys Gly Ser Ser Gly Gly Pro Leu Leu Cys Pro Ser Gly His Ala
        275                 280                 285

Val Gly Ile Phe Arg Ala Ala Val Cys Thr Arg Gly Val Ala Lys Ala
    290                 295                 300

Val Asp Phe Ile Pro Val Glu Ser Met Glu Thr Thr Met Arg Thr Ser
305                 310                 315                 320

Ser Ala Trp Arg His Pro Gln Phe Gly Gly Lys Lys Lys
            325                 330

<210> SEQ ID NO 5
<211> LENGTH: 20
<212> TYPE: DNA
<213> ORGANISM: HCV

<400> SEQUENCE: 5
ccatggaccg ggagatggct                                              20

<210> SEQ ID NO 6
<211> LENGTH: 63
<212> TYPE: DNA
<213> ORGANISM: HCV

<400> SEQUENCE: 6
ggatccttaa ccaccgaact gcgggtgacg ccaagcgcta ctagtccgca tggtagtttc    60
cat                                                                 63

<210> SEQ ID NO 7
<211> LENGTH: 46
<212> TYPE: DNA
<213> ORGANISM: HCV

<400> SEQUENCE: 7
gctcgagcat caccatcacc atcacactag tgcaggcata accaaa                  46

<210> SEQ ID NO 8
<211> LENGTH: 45
<212> TYPE: DNA
<213> ORGANISM: HCV

<400> SEQUENCE: 8
aacaatggat ccttactttt tcttttttacc accgaactgc gggtg                  45

<210> SEQ ID NO 9
<211> LENGTH: 45
<212> TYPE: DNA
<213> ORGANISM: HCV

<400> SEQUENCE: 9
acctgccata tgaaaagaa aaagctcgag catcaccatc accat                    45

<210> SEQ ID NO 10
<211> LENGTH: 303
<212> TYPE: PRT
<213> ORGANISM: HCV

<400> SEQUENCE: 10

Ala Gly Ile Thr Lys Val Pro Tyr Phe Val Arg Ala Gln Gly Leu Ile
1               5                   10                  15

Arg Ala Cys Met Leu Val Arg Lys Ala Ala Gly Gly His Tyr Val Gln
            20                  25                  30

Met Ala Phe Met Lys Leu Ala Ala Leu Thr Gly Thr Tyr Val Tyr Asp
```

-continued

```
                35                  40                  45
His Leu Thr Pro Leu Gln Asp Trp Ala His Ala Gly Leu Arg Asp Leu
 50                  55                  60

Ala Val Ala Val Glu Pro Val Ile Phe Ser Asp Met Glu Val Lys Ile
 65                  70                  75                  80

Ile Thr Trp Gly Ala Asp Thr Ala Ala Cys Gly Asp Ile Ile Ser Gly
                 85                  90                  95

Leu Pro Val Ser Ala Arg Arg Gly Arg Glu Ile Leu Leu Gly Pro Ala
                100                 105                 110

Asp Asn Phe Glu Gly Gln Gly Trp Arg Leu Leu Ala Pro Ile Thr Ala
            115                 120                 125

Tyr Ser Gln Gln Thr Arg Gly Leu Leu Gly Cys Ile Ile Thr Ser Leu
    130                 135                 140

Thr Gly Arg Asp Lys Asn Gln Val Glu Gly Glu Val Gln Val Val Ser
145                 150                 155                 160

Thr Ala Thr Gln Ser Phe Leu Ala Thr Cys Val Asn Gly Val Cys Trp
                165                 170                 175

Thr Val Phe His Gly Ala Gly Ser Lys Thr Leu Ala Gly Pro Lys Gly
                180                 185                 190

Pro Ile Thr Gln Met Tyr Thr Asn Val Asp Gln Asp Leu Val Gly Trp
            195                 200                 205

Gln Ala Pro Pro Gly Ala Arg Ser Met Thr Pro Cys Thr Cys Gly Ser
    210                 215                 220

Ser Asp Leu Tyr Leu Val Thr Arg His Ala Asp Val Ile Pro Val Arg
225                 230                 235                 240

Arg Arg Gly Asp Ser Arg Gly Ser Leu Leu Ser Pro Arg Pro Val Ser
                245                 250                 255

Tyr Leu Lys Gly Ser Ser Gly Gly Pro Leu Leu Cys Pro Ser Gly His
                260                 265                 270

Ala Val Gly Ile Phe Arg Ala Ala Val Cys Thr Arg Gly Val Ala Lys
            275                 280                 285

Ala Val Asp Phe Ile Pro Val Glu Ser Met Glu Thr Thr Met Arg
    290                 295                 300
```

<210> SEQ ID NO 11
<211> LENGTH: 393
<212> TYPE: PRT
<213> ORGANISM: HCV

<400> SEQUENCE: 11

```
Met Ala Ala Ser Cys Gly Gly Ala Val Phe Ile Gly Leu Ala Leu Leu
 1               5                  10                  15

Thr Leu Ser Pro Tyr Tyr Lys Val Leu Leu Ala Arg Leu Ile Trp Trp
                20                  25                  30

Leu Gln Tyr Leu Ile Thr Arg Val Glu Ala His Leu Gln Val Trp Ile
            35                  40                  45

Pro Pro Leu Asn Val Arg Gly Gly Arg Asp Ala Ile Ile Leu Leu Thr
    50                  55                  60

Cys Ala Val His Pro Glu Leu Ile Phe Asp Ile Thr Lys Leu Leu Leu
 65                  70                  75                  80

Ala Ile Phe Gly Pro Leu Met Val Leu Gln Ala Gly Ile Thr Lys Val
                 85                  90                  95

Pro Tyr Phe Val Arg Ala Gln Gly Leu Ile Arg Ala Cys Met Leu Val
                100                 105                 110
```

```
Arg Lys Ala Ala Gly Gly His Tyr Val Gln Met Ala Phe Met Lys Leu
        115                 120                 125

Ala Ala Leu Thr Gly Thr Tyr Val Tyr Asp His Leu Thr Pro Leu Gln
    130                 135                 140

Asp Trp Ala His Ala Gly Leu Arg Asp Leu Ala Val Ala Val Glu Pro
145                 150                 155                 160

Val Ile Phe Ser Asp Met Glu Val Lys Ile Ile Thr Trp Gly Ala Asp
                165                 170                 175

Thr Ala Ala Cys Gly Asp Ile Ile Ser Gly Leu Pro Val Ser Ala Arg
            180                 185                 190

Arg Gly Arg Glu Ile Leu Leu Gly Pro Ala Asp Asn Phe Glu Gly Gln
        195                 200                 205

Gly Trp Arg Leu Leu Ala Pro Ile Thr Ala Tyr Ser Gln Gln Thr Arg
    210                 215                 220

Gly Leu Leu Gly Cys Ile Ile Thr Ser Leu Thr Gly Arg Asp Lys Asn
225                 230                 235                 240

Gln Val Glu Gly Glu Val Gln Val Val Ser Thr Ala Thr Gln Ser Phe
                245                 250                 255

Leu Ala Thr Cys Val Asn Gly Val Cys Trp Thr Val Phe His Gly Ala
            260                 265                 270

Gly Ser Lys Thr Leu Ala Gly Pro Lys Gly Pro Ile Thr Gln Met Tyr
        275                 280                 285

Thr Asn Val Asp Gln Asp Leu Val Gly Trp Gln Ala Pro Pro Gly Ala
    290                 295                 300

Arg Ser Met Thr Pro Cys Thr Cys Gly Ser Ser Asp Leu Tyr Leu Val
305                 310                 315                 320

Thr Arg His Ala Asp Val Ile Pro Val Arg Arg Arg Gly Asp Ser Arg
                325                 330                 335

Gly Ser Leu Leu Ser Pro Arg Pro Val Ser Tyr Leu Lys Gly Ser Ser
            340                 345                 350

Gly Gly Pro Leu Leu Cys Pro Ser Gly His Ala Val Gly Ile Phe Arg
        355                 360                 365

Ala Ala Val Cys Thr Arg Gly Val Ala Lys Ala Val Asp Phe Ile Pro
    370                 375                 380

Val Glu Ser Met Glu Thr Thr Met Arg
385                 390

<210> SEQ ID NO 12
<211> LENGTH: 380
<212> TYPE: PRT
<213> ORGANISM: HCV

<400> SEQUENCE: 12

Ala Leu Leu Thr Leu Ser Pro Tyr Tyr Lys Val Leu Leu Ala Arg Leu
1               5                   10                  15

Ile Trp Trp Leu Gln Tyr Leu Ile Thr Arg Val Glu Ala His Leu Gln
                20                  25                  30

Val Trp Ile Pro Pro Leu Asn Val Arg Gly Gly Arg Asp Ala Ile Ile
            35                  40                  45

Leu Leu Thr Cys Ala Val His Pro Glu Leu Ile Phe Asp Ile Thr Lys
    50                  55                  60

Leu Leu Leu Ala Ile Phe Gly Pro Leu Met Val Leu Gln Ala Gly Ile
65                  70                  75                  80

Thr Lys Val Pro Tyr Phe Val Arg Ala Gln Gly Leu Ile Arg Ala Cys
                85                  90                  95
```

```
Met Leu Val Arg Lys Ala Ala Gly Gly His Tyr Val Gln Met Ala Phe
            100                 105                 110

Met Lys Leu Ala Ala Leu Thr Gly Thr Tyr Val Tyr Asp His Leu Thr
            115                 120                 125

Pro Leu Gln Asp Trp Ala His Ala Gly Leu Arg Asp Leu Ala Val Ala
            130                 135                 140

Val Glu Pro Val Ile Phe Ser Asp Met Glu Val Lys Ile Ile Thr Trp
145                 150                 155                 160

Gly Ala Asp Thr Ala Ala Cys Gly Asp Ile Ile Ser Gly Leu Pro Val
                165                 170                 175

Ser Ala Arg Arg Gly Arg Glu Ile Leu Leu Gly Pro Ala Asp Asn Phe
            180                 185                 190

Glu Gly Gln Gly Trp Arg Leu Leu Ala Pro Ile Thr Ala Tyr Ser Gln
            195                 200                 205

Gln Thr Arg Gly Leu Leu Gly Cys Ile Ile Thr Ser Leu Thr Gly Arg
            210                 215                 220

Asp Lys Asn Gln Val Glu Gly Glu Val Gln Val Val Ser Thr Ala Thr
225                 230                 235                 240

Gln Ser Phe Leu Ala Thr Cys Val Asn Gly Val Cys Trp Thr Val Phe
                245                 250                 255

His Gly Ala Gly Ser Lys Thr Leu Ala Gly Pro Lys Gly Pro Ile Thr
            260                 265                 270

Gln Met Tyr Thr Asn Val Asp Gln Asp Leu Val Gly Trp Gln Ala Pro
            275                 280                 285

Pro Gly Ala Arg Ser Met Thr Pro Cys Thr Cys Gly Ser Ser Asp Leu
            290                 295                 300

Tyr Leu Val Thr Arg His Ala Asp Val Ile Pro Val Arg Arg Arg Gly
305                 310                 315                 320

Asp Ser Arg Gly Ser Leu Leu Ser Pro Arg Pro Val Ser Tyr Leu Lys
                325                 330                 335

Gly Ser Ser Gly Gly Pro Leu Leu Cys Pro Ser Gly His Ala Val Gly
            340                 345                 350

Ile Phe Arg Ala Ala Val Cys Thr Arg Gly Val Ala Lys Ala Val Asp
            355                 360                 365

Phe Ile Pro Val Glu Ser Met Glu Thr Thr Met Arg
            370                 375                 380

<210> SEQ ID NO 13
<211> LENGTH: 352
<212> TYPE: PRT
<213> ORGANISM: HCV

<400> SEQUENCE: 13

Ala His Leu Gln Val Trp Ile Pro Pro Leu Asn Val Arg Gly Gly Arg
1               5                   10                  15

Asp Ala Ile Ile Leu Leu Thr Cys Ala Val His Pro Glu Leu Ile Phe
            20                  25                  30

Asp Ile Thr Lys Leu Leu Leu Ala Ile Phe Gly Pro Leu Met Val Leu
            35                  40                  45

Gln Ala Gly Ile Thr Lys Val Pro Tyr Phe Val Arg Ala Gln Gly Leu
            50                  55                  60

Ile Arg Ala Cys Met Leu Val Arg Lys Ala Ala Gly His Tyr Val
65                  70                  75                  80

Gln Met Ala Phe Met Lys Leu Ala Ala Leu Thr Gly Thr Tyr Val Tyr
```

```
                85                  90                  95
Asp His Leu Thr Pro Leu Gln Asp Trp Ala His Ala Gly Leu Arg Asp
            100                 105                 110
Leu Ala Val Ala Val Glu Pro Val Ile Phe Ser Asp Met Glu Val Lys
        115                 120                 125
Ile Ile Thr Trp Gly Ala Asp Thr Ala Ala Cys Gly Asp Ile Ile Ser
    130                 135                 140
Gly Leu Pro Val Ser Ala Arg Arg Gly Arg Glu Ile Leu Leu Gly Pro
145                 150                 155                 160
Ala Asp Asn Phe Glu Gly Gln Gly Trp Arg Leu Leu Ala Pro Ile Thr
                165                 170                 175
Ala Tyr Ser Gln Gln Thr Arg Gly Leu Leu Gly Cys Ile Ile Thr Ser
            180                 185                 190
Leu Thr Gly Arg Asp Lys Asn Gln Val Glu Gly Glu Val Gln Val Val
        195                 200                 205
Ser Thr Ala Thr Gln Ser Phe Leu Ala Thr Cys Val Asn Gly Val Cys
    210                 215                 220
Trp Thr Val Phe His Gly Ala Gly Ser Lys Thr Leu Ala Gly Pro Lys
225                 230                 235                 240
Gly Pro Ile Thr Gln Met Tyr Thr Asn Val Asp Gln Asp Leu Val Gly
                245                 250                 255
Trp Gln Ala Pro Pro Gly Ala Arg Ser Met Thr Pro Cys Thr Cys Gly
            260                 265                 270
Ser Ser Asp Leu Tyr Leu Val Thr Arg His Ala Asp Val Ile Pro Val
        275                 280                 285
Arg Arg Arg Gly Asp Ser Arg Gly Ser Leu Leu Ser Pro Arg Pro Val
    290                 295                 300
Ser Tyr Leu Lys Gly Ser Ser Gly Gly Pro Leu Leu Cys Pro Ser Gly
305                 310                 315                 320
His Ala Val Gly Ile Phe Arg Ala Ala Val Cys Thr Arg Gly Val Ala
                325                 330                 335
Lys Ala Val Asp Phe Ile Pro Val Glu Ser Met Glu Thr Thr Met Arg
            340                 345                 350

<210> SEQ ID NO 14
<211> LENGTH: 341
<212> TYPE: PRT
<213> ORGANISM: HCV

<400> SEQUENCE: 14

Val Arg Gly Gly Arg Asp Ala Ile Ile Leu Leu Thr Cys Ala Val His
1               5                   10                  15
Pro Glu Leu Ile Phe Asp Ile Thr Lys Leu Leu Leu Ala Ile Phe Gly
            20                  25                  30
Pro Leu Met Val Leu Gln Ala Gly Ile Thr Lys Val Pro Tyr Phe Val
        35                  40                  45
Arg Ala Gln Gly Leu Ile Arg Ala Cys Met Leu Val Arg Lys Ala Ala
    50                  55                  60
Gly Gly His Tyr Val Gln Met Ala Phe Met Lys Leu Ala Ala Leu Thr
65                  70                  75                  80
Gly Thr Tyr Val Tyr Asp His Leu Thr Pro Leu Gln Asp Trp Ala His
                85                  90                  95
Ala Gly Leu Arg Asp Leu Ala Val Ala Val Glu Pro Val Ile Phe Ser
            100                 105                 110
```

```
Asp Met Glu Val Lys Ile Ile Thr Trp Gly Ala Asp Thr Ala Ala Cys
            115                 120                 125

Gly Asp Ile Ile Ser Gly Leu Pro Val Ser Ala Arg Arg Gly Arg Glu
        130                 135                 140

Ile Leu Leu Gly Pro Ala Asp Asn Phe Glu Gly Gln Gly Trp Arg Leu
145                 150                 155                 160

Leu Ala Pro Ile Thr Ala Tyr Ser Gln Gln Thr Arg Gly Leu Leu Gly
                165                 170                 175

Cys Ile Ile Thr Ser Leu Thr Gly Arg Asp Lys Asn Gln Val Glu Gly
            180                 185                 190

Glu Val Gln Val Val Ser Thr Ala Thr Gln Ser Phe Leu Ala Thr Cys
        195                 200                 205

Val Asn Gly Val Cys Trp Thr Val Phe His Gly Ala Gly Ser Lys Thr
    210                 215                 220

Leu Ala Gly Pro Lys Gly Pro Ile Thr Gln Met Tyr Thr Asn Val Asp
225                 230                 235                 240

Gln Asp Leu Val Gly Trp Gln Ala Pro Pro Gly Ala Arg Ser Met Thr
                245                 250                 255

Pro Cys Thr Cys Gly Ser Ser Asp Leu Tyr Leu Val Thr Arg His Ala
            260                 265                 270

Asp Val Ile Pro Val Arg Arg Arg Gly Asp Ser Arg Gly Ser Leu Leu
        275                 280                 285

Ser Pro Arg Pro Val Ser Tyr Leu Lys Gly Ser Ser Gly Gly Pro Leu
    290                 295                 300

Leu Cys Pro Ser Gly His Ala Val Gly Ile Phe Arg Ala Ala Val Cys
305                 310                 315                 320

Thr Arg Gly Val Ala Lys Ala Val Asp Phe Ile Pro Val Glu Ser Met
                325                 330                 335

Glu Thr Thr Met Arg
                340

<210> SEQ ID NO 15
<211> LENGTH: 292
<212> TYPE: PRT
<213> ORGANISM: HCV

<400> SEQUENCE: 15

Ala Gln Gly Leu Ile Arg Ala Cys Met Leu Val Arg Lys Ala Ala Gly
1               5                   10                  15

Gly His Tyr Val Gln Met Ala Phe Met Lys Leu Ala Ala Leu Thr Gly
                20                  25                  30

Thr Tyr Val Tyr Asp His Leu Thr Pro Leu Gln Asp Trp Ala His Ala
            35                  40                  45

Gly Leu Arg Asp Leu Ala Val Ala Val Glu Pro Val Ile Phe Ser Asp
        50                  55                  60

Met Glu Val Lys Ile Ile Thr Trp Gly Ala Asp Thr Ala Ala Cys Gly
65                  70                  75                  80

Asp Ile Ile Ser Gly Leu Pro Val Ser Ala Arg Arg Gly Arg Glu Ile
                85                  90                  95

Leu Leu Gly Pro Ala Asp Asn Phe Glu Gly Gln Gly Trp Arg Leu Leu
            100                 105                 110

Ala Pro Ile Thr Ala Tyr Ser Gln Gln Thr Arg Gly Leu Leu Gly Cys
        115                 120                 125

Ile Ile Thr Ser Leu Thr Gly Arg Asp Lys Asn Gln Val Glu Gly Glu
    130                 135                 140
```

-continued

```
Val Gln Val Val Ser Thr Ala Thr Gln Ser Phe Leu Ala Thr Cys Val
145                 150                 155                 160

Asn Gly Val Cys Trp Thr Val Phe His Gly Ala Gly Ser Lys Thr Leu
            165                 170                 175

Ala Gly Pro Lys Gly Pro Ile Thr Gln Met Tyr Thr Asn Val Asp Gln
            180                 185                 190

Asp Leu Val Gly Trp Gln Ala Pro Pro Gly Ala Arg Ser Met Thr Pro
            195                 200                 205

Cys Thr Cys Gly Ser Ser Asp Leu Tyr Leu Val Thr Arg His Ala Asp
            210                 215                 220

Val Ile Pro Val Arg Arg Arg Gly Asp Ser Arg Gly Ser Leu Leu Ser
225                 230                 235                 240

Pro Arg Pro Val Ser Tyr Leu Lys Gly Ser Ser Gly Gly Pro Leu Leu
                245                 250                 255

Cys Pro Ser Gly His Ala Val Gly Ile Phe Arg Ala Ala Val Cys Thr
            260                 265                 270

Arg Gly Val Ala Lys Ala Val Asp Phe Ile Pro Val Glu Ser Met Glu
            275                 280                 285

Thr Thr Met Arg
        290

<210> SEQ ID NO 16
<211> LENGTH: 303
<212> TYPE: PRT
<213> ORGANISM: HCV

<400> SEQUENCE: 16

Ala Gly Ile Thr Lys Val Pro Tyr Phe Val Arg Ala Gln Gly Leu Ile
1               5                   10                  15

Arg Ala Cys Met Leu Val Arg Lys Ala Ala Gly Gly His Tyr Val Gln
            20                  25                  30

Met Ala Phe Met Lys Leu Ala Ala Leu Thr Gly Thr Tyr Val Tyr Asp
            35                  40                  45

Ala Leu Thr Pro Leu Gln Asp Trp Ala His Ala Gly Leu Arg Asp Leu
50                  55                  60

Ala Val Ala Val Glu Pro Val Ile Phe Ser Asp Met Glu Val Lys Ile
65                  70                  75                  80

Ile Thr Trp Gly Ala Asp Thr Ala Ala Cys Gly Asp Ile Ile Ser Gly
                85                  90                  95

Leu Pro Val Ser Ala Arg Arg Gly Arg Glu Ile Leu Leu Gly Pro Ala
            100                 105                 110

Asp Asn Phe Glu Gly Gln Gly Trp Arg Leu Leu Ala Pro Ile Thr Ala
            115                 120                 125

Tyr Ser Gln Gln Thr Arg Gly Leu Leu Gly Cys Ile Ile Thr Ser Leu
            130                 135                 140

Thr Gly Arg Asp Lys Asn Gln Val Glu Gly Glu Val Gln Val Val Ser
145                 150                 155                 160

Thr Ala Thr Gln Ser Phe Leu Ala Thr Cys Val Asn Gly Val Cys Trp
                165                 170                 175

Thr Val Phe His Gly Ala Gly Ser Lys Thr Leu Ala Gly Pro Lys Gly
            180                 185                 190

Pro Ile Thr Gln Met Tyr Thr Asn Val Asp Gln Asp Leu Val Gly Trp
            195                 200                 205

Gln Ala Pro Pro Gly Ala Arg Ser Met Thr Pro Cys Thr Cys Gly Ser
```

```
        210                 215                 220
Ser Asp Leu Tyr Leu Val Thr Arg His Ala Asp Val Ile Pro Val Arg
225                 230                 235                 240

Arg Arg Gly Asp Ser Arg Gly Ser Leu Leu Ser Pro Arg Pro Val Ser
                245                 250                 255

Tyr Leu Lys Gly Ser Ser Gly Gly Pro Leu Leu Cys Pro Ser Gly His
                260                 265                 270

Ala Val Gly Ile Phe Arg Ala Ala Val Cys Thr Arg Gly Val Ala Lys
                275                 280                 285

Ala Val Asp Phe Ile Pro Val Glu Ser Met Glu Thr Thr Met Arg
                290                 295                 300

<210> SEQ ID NO 17
<211> LENGTH: 301
<212> TYPE: PRT
<213> ORGANISM: HCV

<400> SEQUENCE: 17

Ala Gly Ile Thr Lys Val Pro Tyr Phe Val Arg Ala Gln Gly Leu Ile
1               5                   10                  15

Arg Ala Cys Met Leu Val Arg Lys Ala Ala Gly Gly His Tyr Val Gln
                20                  25                  30

Met Ala Phe Met Lys Leu Ala Ala Leu Thr Gly Thr Tyr Val Tyr Asp
                35                  40                  45

His Leu Thr Pro Leu Gln Asp Trp Ala His Ala Gly Leu Arg Asp Leu
            50                  55                  60

Ala Val Ala Val Glu Pro Val Ile Phe Ser Asp Met Glu Val Lys Ile
65                  70                  75                  80

Ile Thr Trp Gly Ala Asp Thr Ala Ala Cys Gly Asp Ile Ile Ser Gly
                85                  90                  95

Leu Pro Val Ser Ala Arg Arg Gly Arg Glu Ile Leu Leu Gly Pro Ala
                100                 105                 110

Asp Asn Phe Glu Gly Gln Gly Trp Arg Leu Pro Ile Thr Ala Tyr Ser
            115                 120                 125

Gln Gln Thr Arg Gly Leu Leu Gly Cys Ile Ile Thr Ser Leu Thr Gly
130                 135                 140

Arg Asp Lys Asn Gln Val Glu Gly Glu Val Gln Val Val Ser Thr Ala
145                 150                 155                 160

Thr Gln Ser Phe Leu Ala Thr Cys Val Asn Gly Val Cys Trp Thr Val
                165                 170                 175

Phe His Gly Ala Gly Ser Lys Thr Leu Ala Gly Pro Lys Gly Pro Ile
                180                 185                 190

Thr Gln Met Tyr Thr Asn Val Asp Gln Asp Leu Val Gly Trp Gln Ala
            195                 200                 205

Pro Pro Gly Ala Arg Ser Met Thr Pro Cys Thr Cys Gly Ser Ser Asp
            210                 215                 220

Leu Tyr Leu Val Thr Arg His Ala Asp Val Ile Pro Val Arg Arg
225                 230                 235                 240

Gly Asp Ser Arg Gly Ser Leu Leu Ser Pro Arg Pro Val Ser Tyr Leu
                245                 250                 255

Lys Gly Ser Ser Gly Gly Pro Leu Leu Cys Pro Ser Gly His Ala Val
                260                 265                 270

Gly Ile Phe Arg Ala Ala Val Cys Thr Arg Gly Val Ala Lys Ala Val
                275                 280                 285
```

```
Asp Phe Ile Pro Val Glu Ser Met Glu Thr Thr Met Arg
290                 295                 300

<210> SEQ ID NO 18
<211> LENGTH: 303
<212> TYPE: PRT
<213> ORGANISM: HCV

<400> SEQUENCE: 18

Ala Gly Ile Thr Lys Val Pro Tyr Phe Val Arg Ala Gln Gly Leu Ile
1               5                   10                  15

Arg Ala Cys Met Leu Val Arg Lys Ala Ala Gly Gly His Tyr Val Gln
                20                  25                  30

Met Ala Phe Met Lys Leu Ala Ala Leu Thr Gly Thr Tyr Val Tyr Asp
            35                  40                  45

His Leu Thr Pro Leu Gln Asp Trp Ala His Ala Gly Leu Arg Asp Leu
        50                  55                  60

Ala Val Ala Val Glu Pro Val Ile Phe Ser Asp Met Glu Val Lys Ile
65                  70                  75                  80

Ile Thr Trp Gly Ala Asp Thr Ala Ala Gly Asp Ile Ile Ser Gly
                85                  90                  95

Leu Pro Val Ser Ala Arg Arg Gly Arg Glu Ile Leu Leu Gly Pro Ala
                100                 105                 110

Asp Asn Phe Glu Gly Gln Gly Trp Arg Leu Leu Ala Pro Ile Thr Ala
            115                 120                 125

Tyr Ser Gln Gln Thr Arg Gly Leu Leu Gly Cys Ile Ile Thr Ser Leu
        130                 135                 140

Thr Gly Arg Asp Lys Asn Gln Val Glu Gly Glu Val Gln Val Val Ser
145                 150                 155                 160

Thr Ala Thr Gln Ser Phe Leu Ala Thr Cys Val Asn Gly Val Cys Trp
                165                 170                 175

Thr Val Phe His Gly Ala Gly Ser Lys Thr Leu Ala Gly Pro Lys Gly
                180                 185                 190

Pro Ile Thr Gln Met Tyr Thr Asn Val Asp Gln Asp Leu Val Gly Trp
            195                 200                 205

Gln Ala Pro Gly Ala Arg Ser Met Thr Pro Cys Thr Cys Gly Ser
210                 215                 220

Ser Asp Leu Tyr Leu Val Thr Arg His Ala Asp Val Ile Pro Val Arg
225                 230                 235                 240

Arg Arg Gly Asp Ser Arg Gly Ser Leu Leu Ser Pro Arg Pro Val Ser
                245                 250                 255

Tyr Leu Lys Gly Ser Ser Gly Gly Pro Leu Leu Cys Pro Ser Gly His
            260                 265                 270

Ala Val Gly Ile Phe Arg Ala Ala Val Cys Thr Arg Gly Val Ala Lys
        275                 280                 285

Ala Val Asp Phe Ile Pro Val Glu Ser Met Glu Thr Thr Met Arg
290                 295                 300

<210> SEQ ID NO 19
<211> LENGTH: 11
<212> TYPE: PRT
<213> ORGANISM: HCV
<220> FEATURE:
<221> NAME/KEY: VARIANT
<222> LOCATION: (1)...(1)
<223> OTHER INFORMATION: Asp labeled with anthranilyl
<220> FEATURE:
<221> NAME/KEY: VARIANT
```

```
<222> LOCATION: (6)...(6)
<223> OTHER INFORMATION: Xaa at position 6 is Abu
<220> FEATURE:
<221> NAME/KEY: VARIANT
<222> LOCATION: (6)...(7)
<223> OTHER INFORMATION: Abu-A between 6 and 7 is C(O)-O
<220> FEATURE:
<221> NAME/KEY: VARIANT
<222> LOCATION: (9)...(9)
<223> OTHER INFORMATION: Tyr at position 9 is derivatized with 3-NO2

<400> SEQUENCE: 19

Asp Asp Ile Val Pro Xaa Ala Met Tyr Thr Trp
1               5                   10

<210> SEQ ID NO 20
<211> LENGTH: 6
<212> TYPE: PRT
<213> ORGANISM: HCV
<220> FEATURE:
<221> NAME/KEY: VARIANT
<222> LOCATION: (1)...(1)
<223> OTHER INFORMATION: Asp labeled with anthranilyl
<220> FEATURE:
<221> NAME/KEY: VARIANT
<222> LOCATION: (6)...(6)
<223> OTHER INFORMATION: Xaa at position 6 is Abu

<400> SEQUENCE: 20

Asp Asp Ile Val Pro Xaa
1               5

<210> SEQ ID NO 21
<211> LENGTH: 10
<212> TYPE: PRT
<213> ORGANISM: HCV

<400> SEQUENCE: 21

Ser Phe Glu Gly Gln Gly Trp Arg Leu Leu
1               5                   10

<210> SEQ ID NO 22
<211> LENGTH: 20
<212> TYPE: PRT
<213> ORGANISM: HCV

<400> SEQUENCE: 22

Ser Phe Glu Gly Gln Gly Trp Arg Leu Leu Ala Pro Ile Thr Ala Tyr
1               5                   10                  15

Ser Gln Gln Thr
            20

<210> SEQ ID NO 23
<211> LENGTH: 10
<212> TYPE: PRT
<213> ORGANISM: HCV

<400> SEQUENCE: 23

Ala Pro Ile Thr Ala Tyr Ser Gln Gln Thr
1               5                   10

<210> SEQ ID NO 24
<211> LENGTH: 12
<212> TYPE: PRT
<213> ORGANISM: HCV

<400> SEQUENCE: 24
```

-continued

```
Lys Gly Trp Arg Leu Leu Ala Pro Ile Thr Ala Tyr
1               5                   10

<210> SEQ ID NO 25
<211> LENGTH: 6
<212> TYPE: PRT
<213> ORGANISM: HCV

<400> SEQUENCE: 25

Ala Pro Ile Thr Ala Tyr
1               5
```